(12) United States Patent
Netravali et al.

(10) Patent No.: US 8,541,001 B2
(45) Date of Patent: Sep. 24, 2013

(54) BACTERIAL CELLULOSE BASED 'GREEN' COMPOSITES

(75) Inventors: Anil N. Netravali, Ithaca, NY (US); Kaiyan Qiu, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/321,145

(22) PCT Filed: May 17, 2010

(86) PCT No.: PCT/US2010/035103
§ 371 (c)(1),
(2), (4) Date: Feb. 2, 2012

(87) PCT Pub. No.: WO2010/135234
PCT Pub. Date: Nov. 25, 2010

(65) Prior Publication Data
US 2012/0129228 A1    May 24, 2012

Related U.S. Application Data

(60) Provisional application No. 61/179,257, filed on May 18, 2009.

(51) Int. Cl.
*A01N 61/00* (2006.01)
(52) U.S. Cl.
USPC .................................................. 424/195.18
(58) Field of Classification Search
USPC .................................................. 424/195.18
See application file for complete search history.

(56) References Cited

U.S. PATENT DOCUMENTS

| 5,846,213 A | 12/1998 | Wan |
| 2005/0037082 A1 | 2/2005 | Wan et al. |
| 2008/0064072 A1 | 3/2008 | Wan et al. |

FOREIGN PATENT DOCUMENTS

| EP | 0197969 A1 | 10/1986 |

OTHER PUBLICATIONS

International Search Report and Written Opinion of the International Searching Authority for International Patent Application No. PCT/US10/35103 mailed Jan. 14, 2011 (10 pgs.).
Inernational Preliminary Report on Patentability (Chapter 1 of the PCT) for International Patent Application No. PCT/US10/35103 mailed Dec. 1, 2011 (6 pgs.).
Nakagaito, A.N., "Bacterial celulose: the ultimate nano-scalar cellulose morphology for the production of high-strength composites", 2005 Appl. Phys. A vol. 80 pp. 93-97.
Nam, Sunghyun et al. "Green Composites. I. Physical Properties of Ramie Fibers for Environment-friendly Green Composites", 2006 Fibers and Polymers vol. 7, No. 4, pp. 372-379.
Netravali, A.N., "Cellulose/Soy Protein Based 'Green' Composites", Nov. 2008, National Textile Center Annual Report, NTC Project: F08-CR01, pp. 1-5, Nov. 2008.

*Primary Examiner* — Maryam Monshipouri
(74) *Attorney, Agent, or Firm* — Harris Beach PLLC

(57) ABSTRACT

'Green' composites are fabricated using resins, such as soy-based resins, and reinforced with crystalline high strength bacterial cellulose (BC) fibers. Bacterial cellulose is produced by providing a bacterial cellulose-producing bacterium such as *Acetobacter xylinum*; providing an inexpensive bacteria nutritional medium; culturing the bacterium in the bacteria nutritional medium under conditions to produce bacterial cellulose; and isolating bacterial cellulose produced by cultured bacteria from the bacteria nutritional medium. The bacteria nutritional medium comprises an inexpensive carbon source that is a plant-based seed extract. The seed extract is derived from a plant-based seed comprising soluble sugars.

3 Claims, 9 Drawing Sheets

Figure 1:
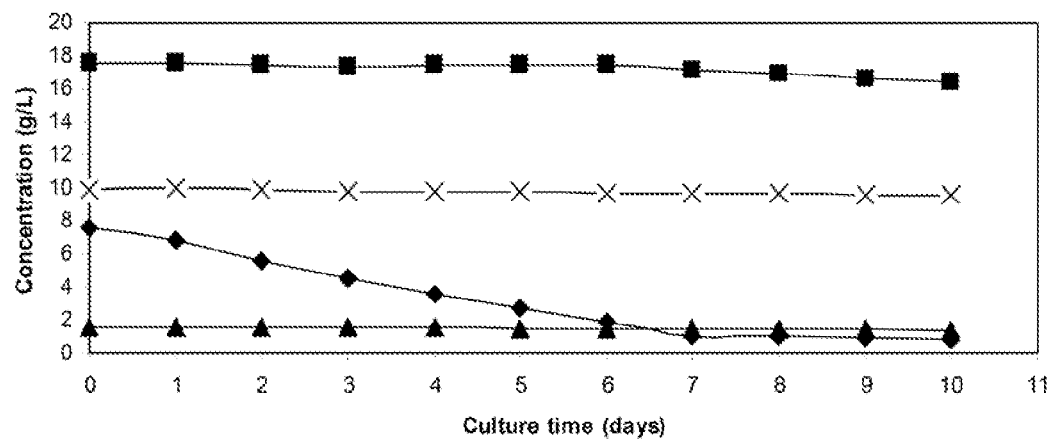

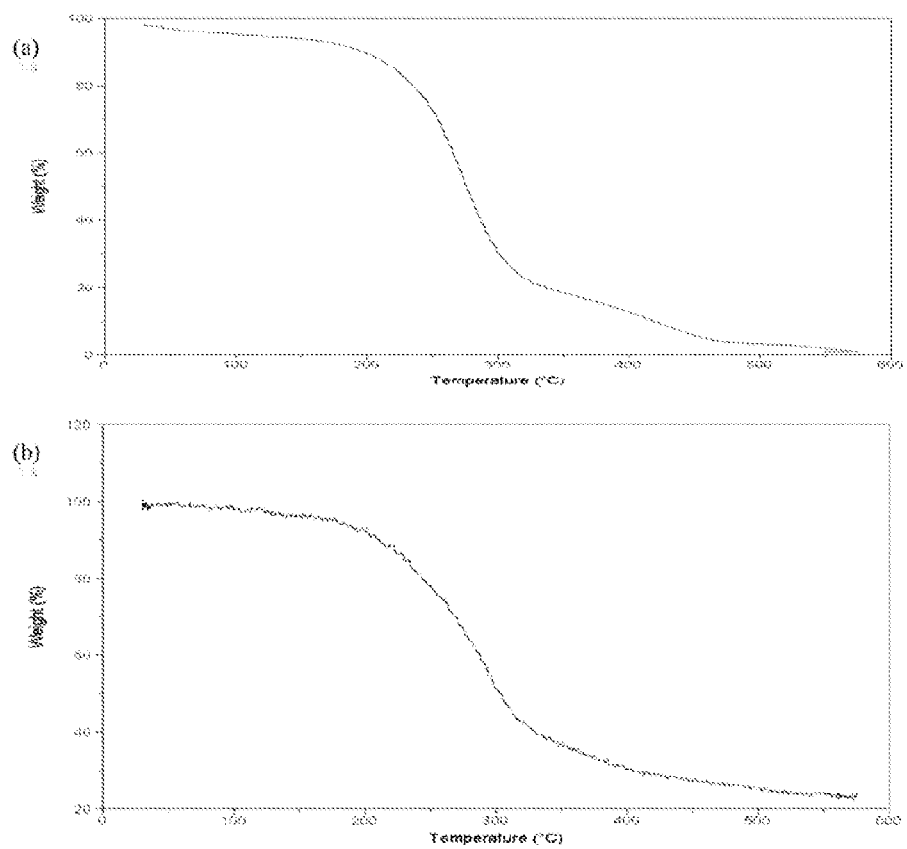
FIGS. 8a-b
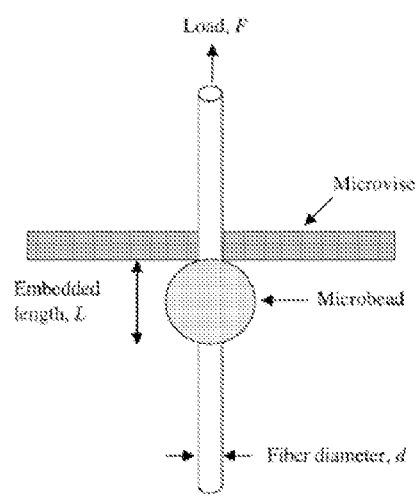
FIG. 9

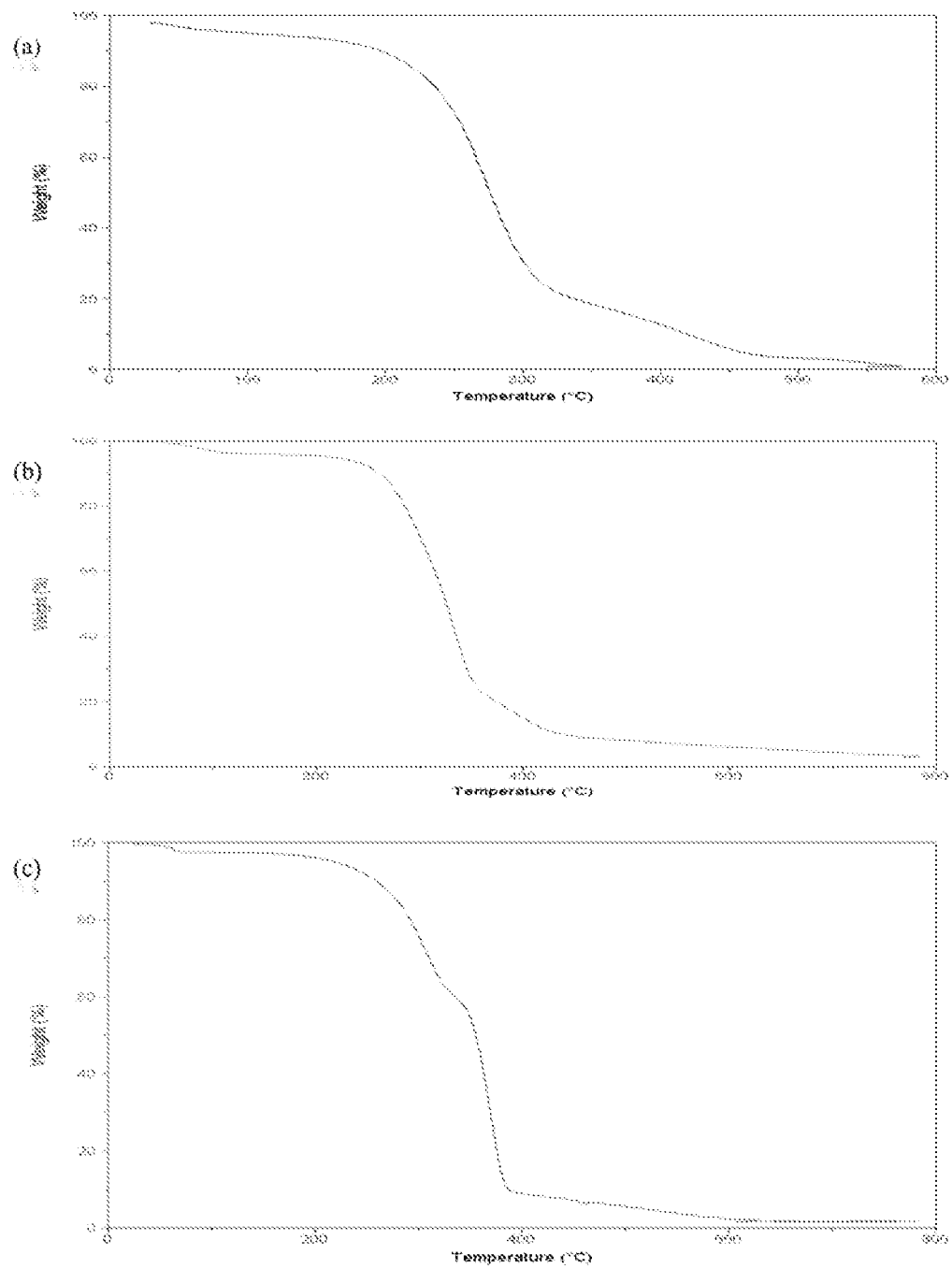
FIGS. 18a-c

BACTERIAL CELLULOSE BASED 'GREEN' COMPOSITES

CROSS-REFERENCE TO RELATED APPLICATIONS

This application is a national stage application under 35 U.S.C. §371 of PCT Application No. PCT/US2010/035103, filed May 17, 2010, which claims priority to and the benefit of U.S. provisional patent application Ser. No. 61/179,257, entitled Bacterial Cellulose Based 'Green' Composites, filed May 18, 2009, which is incorporated herein by reference in its entirety.

STATEMENT REGARDING FEDERALLY SPONSORED RESEARCH OR DEVELOPMENT

The disclosed invention was made with government support under contract no. ITA-08-07400 from the Department of Commerce (National Textile Center). The government has rights in this invention.

1. TECHNICAL FIELD

The invention relates in general to bio-based materials and specifically to bacterial cellulose (BC) and BC based composites. The invention also relates to methods for producing bacterial cellulose (BC) based composites.

2. BACKGROUND OF THE INVENTION

During past several decades, new advanced composites with excellent mechanical properties have been developed and used as metal replacement. However, most composites are made using synthetic non-degradable fibers, such as carbon, aramid and glass and polymers (resins), such as polyetheretherketone (PEEK) and epoxy. They cannot be recycled or reused easily and most end up in landfills. These composites pose a serious solid waste disposal problem due to decreasing landfill space, widespread litter, and pollution of marine environments.

Bacterial cellulose (BC) produced by *Acetobacter xylinum*, is a promising sustainable and biodegradable fibrous material and has the same chemical structure as the plant-based cellulose. However, BC fibers have diameters in the range of a few nano-meters and display many unique properties including higher purity, higher crystallinity, higher degree of polymerization, higher tensile strength, higher modulus and strong biological adaptability (Iguchi, M.; Yamanaka, S.; Budhiono, A. (2000). Bacterial cellulose—a masterpiece of Nature's arts. *Journal of Materials Science,* 35 (2), 261-270; Baeckdahl, H.; Helenius, G.; Bodin, A.; Nannmark, U.; Johansson, B. R.; Risberg, B.; Gatenholm, P. (2006). Mechanical properties of bacterial cellulose and interactions with smooth muscle cells. *Biomaterials,* 27 (9), 2141-2149; Klemm, D.; Schumann, D.; Udhardt, U.; Marsch, S. (2001). Bacterial synthesized cellulose—artificial blood vessels for microsurgery. *Progress in Polymer Science,* 26(9), 1561-1603; Klemm, D.; Heublein, B.; Fink, H. P.; Bohn, Andreas. (2005). Cellulose: Fascinating biopolymer and sustainable raw material. *Angewandte Chemie, International Edition,* 44(22), 3358-3393; Fink, H. P.; Weigel, P.; Purz, H. J.; Ganster, J. (2001). Structure formation of regenerated cellulose materials from NMMO-solutions. *Progress in Polymer Science,* 26(9), 1473-1524). The BC material has been used in a variety of applications including artificial skin and blood vessel, binding agent, loud speaker diaphragms, paper, foods, textile, composite membranes, etc. (Wan et al., 2006; Fontana, J. D.; De Souza, A. M.; Fontana, C. K.; Torriani, I. L.; Moreschi, J. C.; Gallotti, B. J.; De Souza, S. J.; Narcisco, G. P.; Bichara, J. A.; Farah, L. F. X. (1990). Acetobacter cellulose pellicle as a temporary skin substitute. *Applied Biochemistry and Biotechnology,* 24-25, 253-264; Shibazaki, H.; Kuga, S.; Onabe, F.; Usuda, M. (1993). Bacterial cellulose membrane as separation medium. *Journal of Applied Polymer Science,* 50 (6), 965-969; Svensson, A.; Nicklasson, E.; Harrah, T.; Panilaitis, B.; Kaplan, D. L.; Brittberg, M.; Gatenholm, P. (2005) Bacterial cellulose as a potential scaffold for tissue engineering of cartilage. *Biomaterials,* 26 (4), 419-431). Many pure sugars have been used as carbon source for BC culture. Among them mannitol and fructose are the most common and have shown excellent results in terms of BC production (Hong, F.; Qiu, K. (2008). An alternative carbon source from konjac powder for enhancing production of bacterial cellulose in static cultures by a model strain *Acetobacter aceti* subsp. *xylinus* ATCC 23770. *Carbohydrate Polymers,* 72 (3), 545-549). However, cost of these sugars is high and as a result, they are not considered to be ideal for large scale BC production. As a result, many attempts have been made to obtain higher BC yields as well as to reduce the cost of the carbon sources with some success. These include konjac powder hydrolyzate (Hong, F.; Qiu, K. (2008). An alternative carbon source from konjac powder for enhancing production of bacterial cellulose in static cultures by a model strain *Acetobacter aceti* subsp. *xylinus* ATCC 23770. *Carbohydrate Polymers,* 72 (3), 545-549), sugarcane molasses (Keshk, S.; Sameshima, K. (2006). The utilization of sugar cane molasses with/without the presence of lignosulfonate for the production of bacterial cellulose. *Applied Microbiology and Biotechnology,* 72 (2), 291-296), beet molasses (Keshk, S.; Razek, T. Sameshima, K. (2006). Bacterial cellulose production from beet molasses. *African Journal of Biotechnology,* 5(17), 1519-1523) and processed rice bark (Goelzer, F. D. E.; Faria-Tischer, P. C. S.; Vitorino, J. C.; Sierakowski, Maria-R.; Tischer, C. A. Production and characterization of nanospheres of bacterial cellulose from Acetobacter xylinum from processed rice bark. (2009). *Materials Science and Engineering, C: Materials for Biological Applications,* 29(2), 546-551). While some of these sources may be used for industrial BC production in the near future, there is significant scope to further lower the cost of BC production and expand its use in many mass volume applications.

Defatted soy flour (SF) is obtained after extracting oil from the soybeans. It consists mainly of protein (52-54%), sugars (30-32%), dietary fiber (2-3%), minerals and ash (3-6%) and moisture (6-8%). The soybean is a legume species native to East Asia and is classified as an oilseed. It is an annual and economic crop and has been abundantly produced and used in some countries for over 5,000 years (Endres J. G. (2001). Soy protein products: Characteristics, nutritional aspects and utilization, revised and expanded edition. *AOCS Press,* pp. 4-18). Currently, it is an important global crop and provides major amount of edible oil and protein (Martin, H.; Laswai, H.; Kulwa, K. (2010). Nutrient content and acceptability of soybean based complementary food. *African Journal of Food, Agriculture, Nutrition and Development,* 10(1), 2040-2049). The soybean has been shown to contain decent amount of sugars, including fructose, glucose, sucrose, raffinose and stachyose (Giannoccaro, E.; Wang, Y. J.; Chen, P. (2008). Comparison of two HPLC systems and an enzymatic method for quantification of soybean sugars. *Food Chemistry,* 106, 324-330). Fructose, glucose and sucrose have been used as routine carbon sources for BC production in previous reports (Yang et al., 1997). It has also been reported that raffinose and stachyose could be metabolized by lactic acid bacteria (Wang, Y. C.; Yu, R. C.; Yang, H. Y.; Chou, C. C. (2003). Sugar and acid contents in soymilk fermented with lactic acid bacteria alone or simultaneously with bifidobacteria. *Food Microbiology*, 20(3), 333-338). However, BC has not been produced using the soy flour extract (SFE), an inexpensive by-product of SF, as a carbon source by *Acetobacter xylinum*.

There is therefore a need in the art for advanced composites with excellent mechanical properties to use as metal replacements that are sustainable, biodegradable and inexpensive to produce. There is further a need in the art for inexpensive industrial BC production.

3. SUMMARY OF THE INVENTION

A method for producing bacterial cellulose (BC) is provided comprising:
providing a bacterium wherein the bacterium is a bacterial cellulose-producing bacterium;
providing a bacteria nutritional medium;
culturing the bacterium in the bacteria nutritional medium under conditions to produce BC; and
isolating BC produced by cultured bacteria from the bacteria nutritional medium,
wherein:
the bacteria nutritional medium comprises a carbon source,
the carbon source is a plant-based seed extract, and
the plant-based seed extract is derived from a plant-based seed comprising soluble sugars.

Soluble sugars suitable for use in the methods of the invention can include, but are not limited to: fructose, glucose, sucrose, raffinose, stachyose, galactose and maltose. Any seed comprising soluble sugars can be used for the seed extract. Seeds comprising soluble sugars are known in the art.

In one embodiment, the carbon/sugar source is an inexpensive and or sustainable source such as soy flour extract (SFE).

In another embodiment, the bacteria is Acetobacter xylinum.

In another embodiment, the e seed is soy, wheat, corn or a legume.

In another embodiment, the seed extract is soy flour extract (SFE).

In another embodiment, the step of isolating BC comprises harvesting BC pellicles produced on the surface of the bacteria nutritional medium.

In another embodiment, the bacteria nutritional medium comprises microfibrillated cellulose (MFC), nanofibrillated cellulose (NFC), nanoparticles, nanoclay or nanocubes.

In another embodiment, the bacteria nutritional medium comprises fibers.

In another embodiment, the fibers are transparent.

In another embodiment, the fibers comprise a natural cellulose-based or protein-based material.

In another embodiment, the natural cellulose-based material is selected from the group consisting of cotton, linen, flax, sisal, ramie, hemp, kenaf, jute, bamboo, banana, pineapple, kapok and cellulose and combinations thereof.

In another embodiment, the natural protein-based material is selected from the group consisting of wool, silk, angora, cashmere, mohair, alpaca, milk protein and soy protein and combinations thereof.

In another embodiment, the fibers comprise a polymeric material.

In another embodiment, the polymeric material is cellulose acetate, nylon, rayon, modacrylic, olefin, acrylic, polyester, polylactic acid, polylactic-co-glycolic acid (PLGA), polyurethane, aramid (e.g. KEVLAR®), or ultrahigh molecular weight polyethylene, (e.g. SPECTRA® or DYNEEMA®).

In another embodiment, the fibers comprise carbon (e.g., carbon fiber) or glass (e.g., fiberglass). In another embodiment, the fiber is introduced into the nutritional medium before or during the culturing step.

In another embodiment, the method comprises drying or hot-pressing the isolated BC, thereby forming a membrane.

In another embodiment, the method comprises immersing or soaking the isolated BC in a resin.

In another embodiment, the method comprises crosslinking BC and the resin with a crosslinking agent.

In another embodiment, the crosslinking agent is glutaraldehyde (GA), glyoxal, rutin, quercetin, a hydroxyl, a diol or ethylene glycol.

A method for producing a soy flour extract (SFE) for use in the production of bacterial cellulose (BC) is also provided. In one embodiment, the method comprises providing soy flour (e.g., in a powder), preparing a soy flour mixture by mixing the soy flour with water (e.g., at a ratio of 3 parts soy flour:17 parts water); adjusting the pH value of the soy flour mixture to a desired pH (e.g., to pH 4.5 by adding, e.g., hydrochloric acid); heating the soy flour mixture; and filtering the soy flour mixture to remove solid contents (e.g., insoluble protein); evaporating the filtrate to obtain a SFE with a desired sugar concentration.

A method for producing a soy flour extract (SFE) for use in the production of bacterial cellulose (BC) is also provided. The method preferably comprises the step of autoclaving a soy flour extract (SFE). A soy flour extract (SFE) is also provided, for use in the production of bacterial cellulose (BC) and that is enriched for fructose and glucose.

A composition is also provided comprising bacterial cellulose (BC) and a soy-based resin. In one embodiment, the composition comprises 20 to 60% BC by weight.

In another embodiment, the composition is crosslinked.

A composition is also provided comprising bacterial cellulose (BC); and an agent selected from the group consisting of microfibrillated cellulose (MFC), nanofibrillated cellulose (NFC), cellulose nanowhisker, nanoparticle, nanoclay or nanocube, wherein the agent is interwoven or intercalated with the BC. In one embodiment, the composition comprises a resin.

In another embodiment, the resin is transparent.

In another embodiment, the resin is selected from the group consisting of natural resin, plant-based resin and non-toxic resin.

In another embodiment, the resin is biodegradable.

In another embodiment, the resin is water soluble.

In another embodiment, the natural or plant-based resin is a soy-based resin.

In another embodiment, the resin is a petroleum-based resin.

In another embodiment, the petroleum-based resin is an epoxy, vinyl, or unsaturated polyester-based resin.

In another embodiment, the resin is polyethylene oxide (PEO).

In another embodiment, the resin is polyvinyl alcohol (PVA).

In another embodiment, the resin is polyhydroxy alkanoate (PHA).

In another embodiment, the composition is a membrane.

In another embodiment, the composition comprises fibers.

In another embodiment, the fibers are transparent.

In another embodiment, the fibers comprise a natural cellulose-based or protein-based material.

In another embodiment, the natural cellulose-based material is selected from the group consisting of cotton, linen, flax, sisal, ramie, hemp, kenaf, jute, bamboo, banana, pineapple, kapok, and combinations thereof. Any other natural cellulose fibers known in the art can also be used.

In another embodiment, the natural protein-based material is selected from the group consisting of wool, silk, angora, cashmere, mohair, alpaca, milk protein, spider silk, and soy protein and combinations thereof.

In another embodiment, the fibers comprise a polymeric material. In another embodiment, the polymeric material is cellulose acetate, nylon, rayon, modacrylic, olefin, acrylic, polyester, polylactic acid, polylactic-co-glycolic acid (PLGA), polyurethane, aramid (e.g. KEVLAR®), or ultra-high molecular weight polyethylene, (e.g. SPECTRA® or DYNEEMA®). In another embodiment, the fibers comprise carbon (e.g., carbon fiber) or glass (e.g., fiberglass).

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. Consumption of sugars in SFE medium during BC culture by Acetobacter xylinum ATCC 23769. Symbols: ♦, fructose and glucose; ■, sucrose; ▲, raffinose; x, stachyose.

Figure 2:
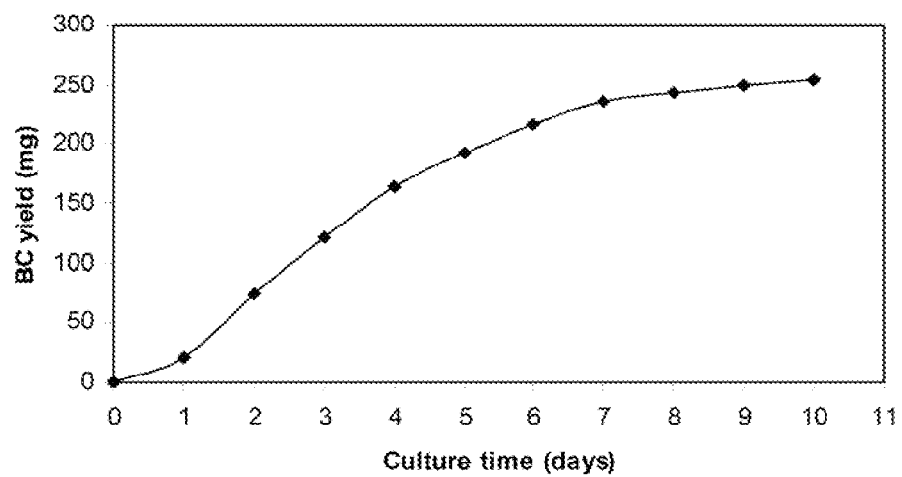

FIG. 2. BC yield in SFE medium during culture.

Figure 3:
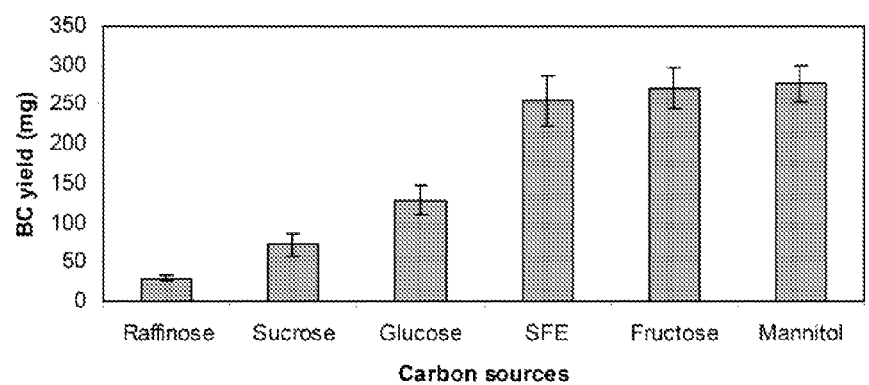

FIG. 3. BC yields obtained for different carbon sources.

Figure 4:
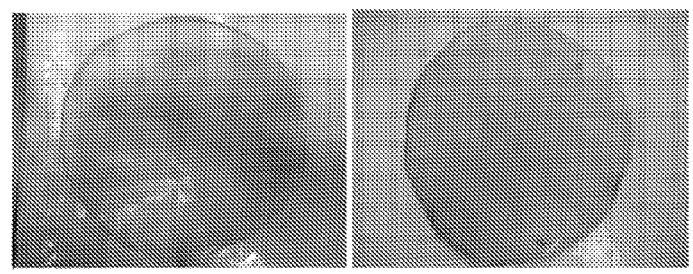

FIG. 4. BC-SPI (left) and GA treated BC-SPI (right) composites.

Figure 5:
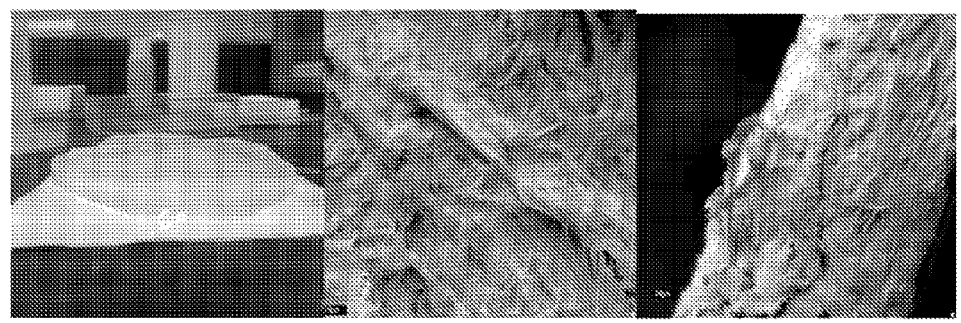

FIG. 5. BC-MFC pellicle (left), SEM images of its surface (middle) and cross section (right).

Figure 6:
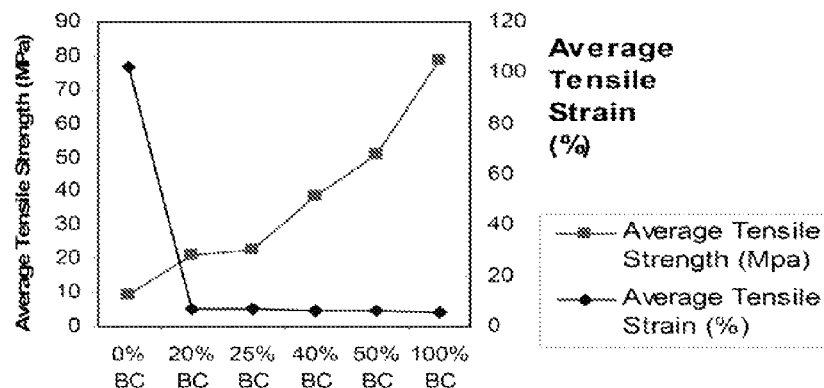

FIG. 6. Tensile properties of BC-soy resin (SPI) composites with different BC contents.

Figure 7:
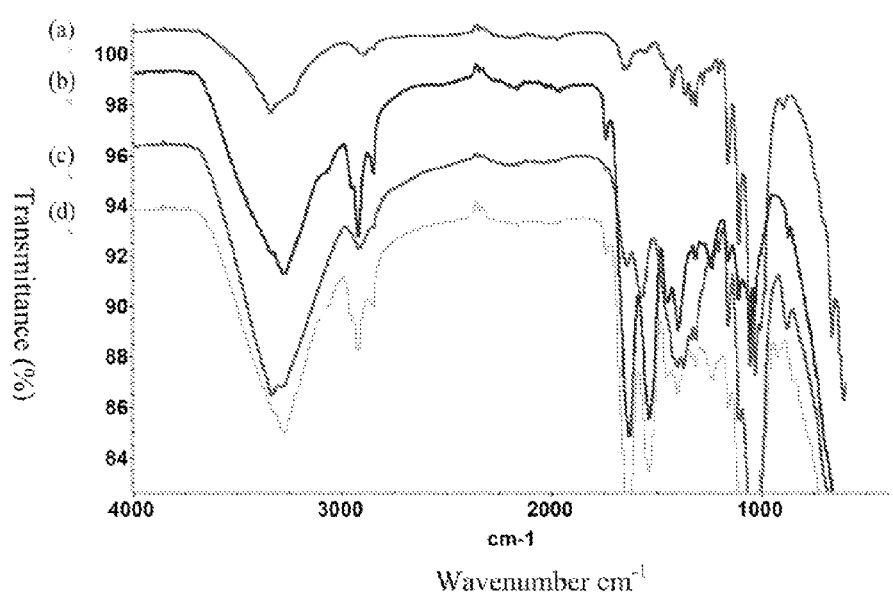

FIG. 7. FTIR spectra of BC, BC-SPI, BC-MFC and BC-MFC-SPI composites (a: BC; b: BC:SPI=1:1; c: BC-MFC; d: BC-MFC:SPI=1:1).

FIGS. 8a-b. TGA of BC and BC-soy resin (SPI) composite. a: BC; b: BC-soy resin (SPI) (1:1).

FIG. 9. Schematic diagram of microbond test.

Figure 10:
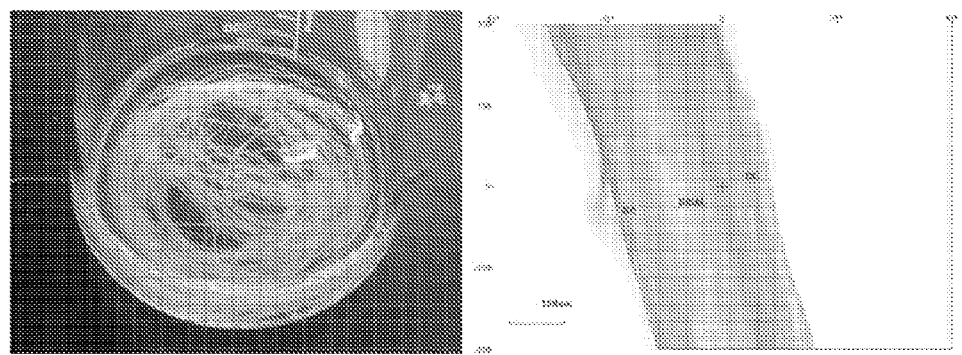

FIG. 10. BC-modified sisal fibers in culture media (left) and microscopic image of a single BC-modified sisal fiber (right).

Figure 11:
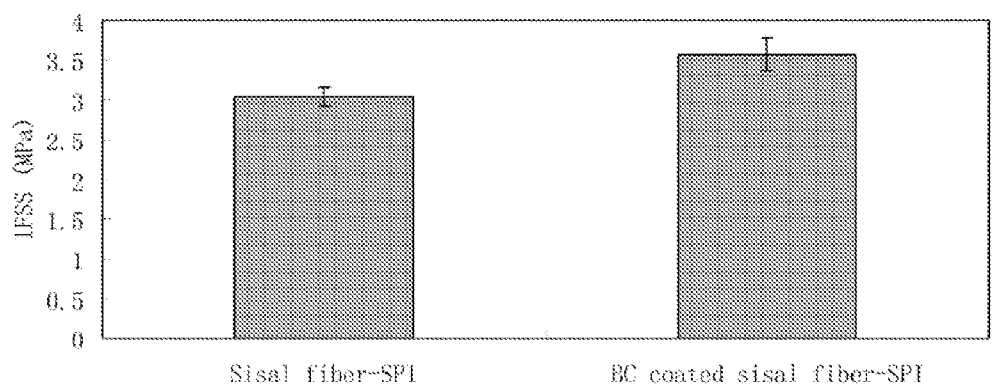

FIG. 11. IFSS of sisal fiber-SPI and BC coated sisal fiber-SPI.

Figure 12:
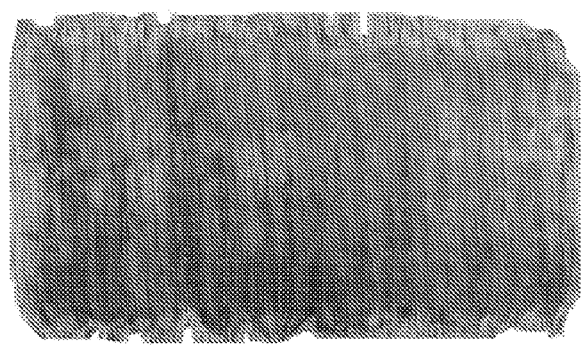

FIG. 12. BC-Sisal-soy resin composites.

Figure 13:
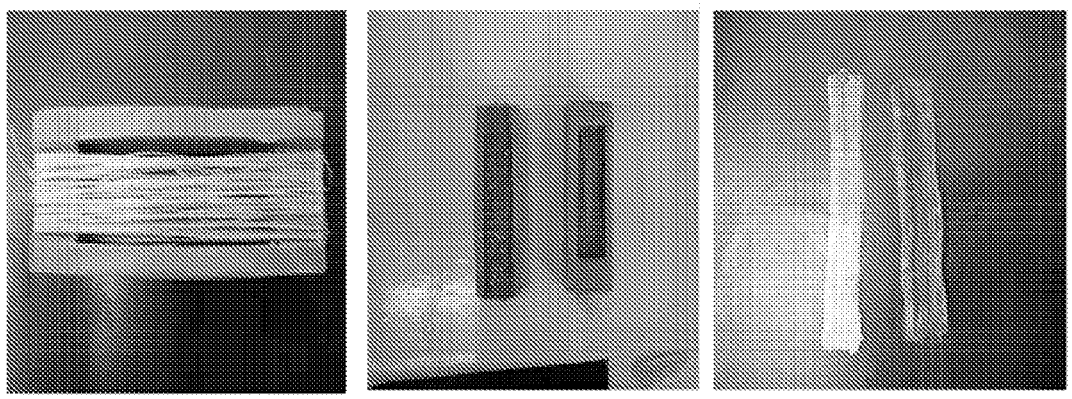

FIG. 13. Example of a silicon mold and its application for aligned BC-Sisal and BC-Sisal-Resin production.

Figure 14:
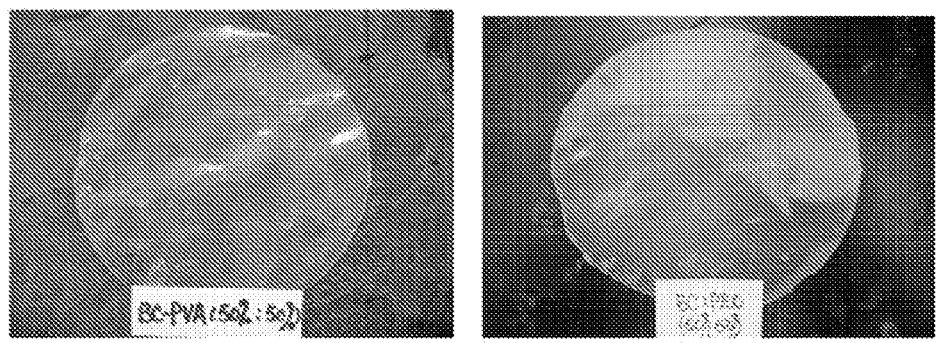

FIG. 14. BC-PVA (left) and BC-PEO (right) composite films.

FIGS. 15a-f. SEM images of BC and BC-PEO composite. a: BC surface morphology. b: BC morphology. c: BC-PVA morphology. d: BC-PVA morphology. e: BC-PEO morphology. f: BC-PEO morphology.

Figure 16:
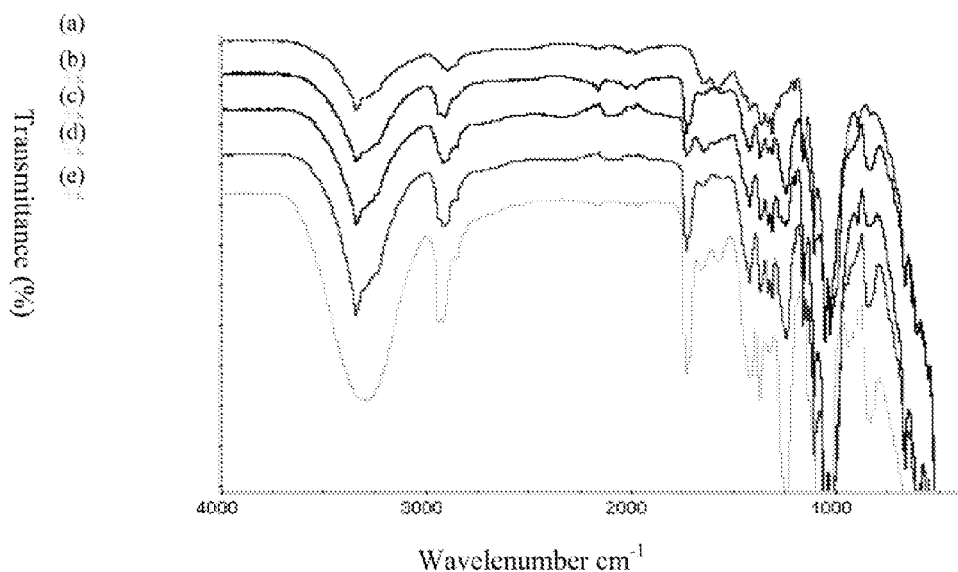

FIG. 16. FTIR spectra of BC, BC-PVA composites and PVA. a: BC; b: BC:PVA=2:1. c: BC:PVA=1:1. d: BC:PVA=1:2. e: PVA.

Figure 17:
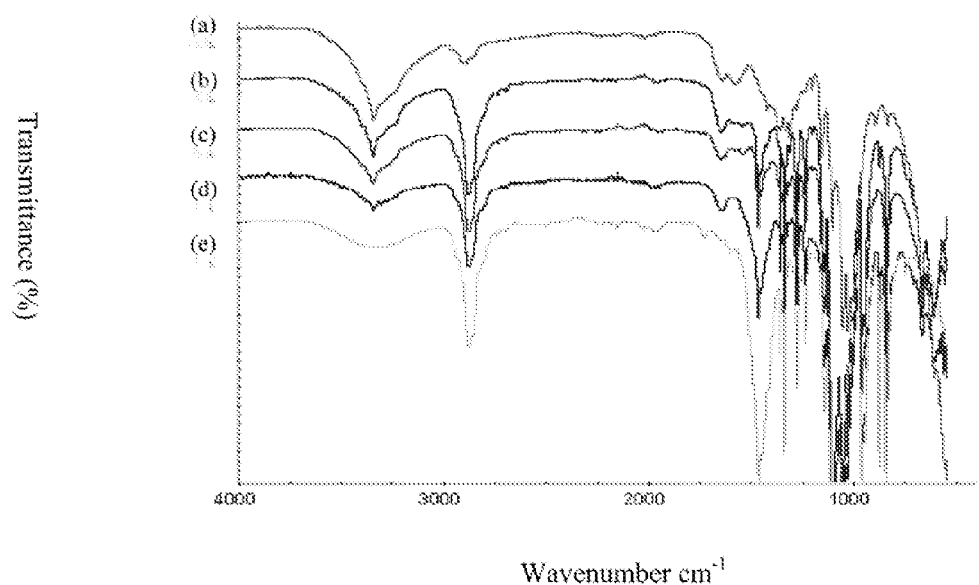

FIG. 17. FTIR spectra of BC, BC-PEO composites and PEO. a: BC. b: BC:PEO=2:1. c: BC:PEO=1:1. d: BC:PEO=1:2. e: PEO.

FIGS. 18a-c. TGA of BC, BC-PVA and BC-PEO composites. a: BC; b: BC-PVA (1:1); c: BC-PEO (1:1).

5. DETAILED DESCRIPTION OF THE INVENTION

Methods are provided for fabricating 'green' composites using resins reinforced with crystalline high strength cellulose fibers. In a specific embodiment, the resin is soy resin. Bacterial cellulose (BC) is a promising biodegradable material with broad potential for composite reinforcement. It is a type of specific cellulose that can be produced by Acetobacter xylinum, a Gram-negative, obligately aerobic bacterium, by culturing Acetobacter xylinum in a nutritional fermentation medium (e.g., at 30° C.) for several days.

In certain embodiments, the nutritional fermentation medium at least contains carbon sources (mannitol, sucrose, fructose, etc.) and nitrogen sources (peptone, tryptone, yeast extract, etc.), and its optimum pH is 5.0.

BC has the same chemical structure as other plant-based cellulose. However, BC is made of fiber diameters of only few nanometers and displays many unique properties including higher purity, higher crystallinity, higher degree of polymerization, higher tensile strength (200-300 MPa), higher modulus (up to 78 GPa) and stronger biological adaptability. BC material is known in the art for use in a variety of applications, including artificial skin and blood vessel, binding agent, loud speaker diaphragms, paper, foods, textile, composite membranes, etc. However, low production rate and high cost of carbon sources have become a bottleneck to BC's industrial production and large scale use.

Methods for using inexpensive carbon sources to produce BC are provided that can be used to reduce the production costs of BC.

BC based 'green' and environment-friendly nano-composites are also provided.

In certain embodiments, additional constituents can be added to the bacteria nutritional medium before or during BC synthesis to further improve the mechanical or properties of the synthesized BC. Micro-fibrillated cellulose (MFC) and/or nano-fibrillated cellulose (NFC) can be added to the bacteria nutritional medium to further improve the mechanical properties of BC. The bacteria excrete a continuous strand of BC as the bacteria take a random walk among the MFC and/or NFC, resulting in an interpenetrating network of BC, MFC and/or NFC. In other embodiments, nanoparticles, nanoclay, nanocubes (e.g., halloysite, aluminosilicate nanotube), cellulose nanowhiskers, etc. can be can be added to the bacteria nutritional medium to improve the mechanical or thermal properties of the synthesized BC. In certain embodiments, the added fibers, nanoparticles, etc. can be transparent. The resulting membrane produced from the BC with the added constituents can have properties similar to a BC membrane alone. However, in certain embodiments, it can be thicker than the BC membrane alone.

In other embodiments, 'green' (e.g., non-toxic, biodegradable), sustainable (derived from renewable resources), or water soluble resins can be added to reduce composite fabrication to a one-step process. Natural fibers such as sisal and ramie can also be added to form hybrid 'green' composites with attractive properties.

BC has several advantages over plant cellulose including: finer structure, no hemicellulose or lignin need to be removed, longer fiber length and greater strength, can be grown to virtually any shape, and can be produced on a variety of substrates For clarity of disclosure, and not by way of limitation, the detailed description of the invention is divided into the subsections set forth below.

5.1 Bacteria and Culture Media for BC Production

Methods are provided herein for producing bacterial cellulose (BC). In one embodiment, the method comprises providing a bacterium wherein the bacterium is a bacterial cellulose-producing bacterium; providing a bacteria nutritional medium; culturing the bacterium in the bacteria nutritional medium under conditions to produce BC; and isolating BC produced by cultured bacteria from the bacteria nutritional medium, wherein: the bacteria nutritional medium comprises a carbon source, the carbon source is a plant-based seed extract, and the plant-based seed extract is derived from a plant-based seed comprising soluble sugars.

Many strains of bacteria that synthesize cellulose can be used to synthesize BC. In a preferred embodiment, *Acetobacter xylinum*, ATCC 23769, can be used (American Type Culture Collection (ATCC), Manassas, Va.).

The bacteria can be maintained using standard culture conditions on agar plates.

Any culture medium known in the art to support the selected bacteria can be used. For example, SFE medium used for BC production can consist of 5 g/L yeast extract, 5 g/L tryptone and autoclaved SFE as the sole carbon source.

Culture media that can be used can consist of 5-50 g/L of one or more carbon sources (e.g., stachyose, raffinose, glucose, sucrose, fructose, mannitol, galactose, maltose), 5 g/L yeast extract and 5 g/L tryptone. In one embodiment, 25 g/L is used. Any small sugar known in the art can also be used.

Bacteria can be maintained using standard culture methods, such as on agar plates containing 25 g/L D-mannitol, 5 g/L yeast extract and 5 g/L tryptone and 20 g/L agar. The mannitol culture medium used for BC production can consist of, for example, 25 g/L D-mannitol, 5 g/L yeast extract and 5 g/L tryptone.

5.2 Bacterial Cellulose (BC) Pellicle Production

The step of culturing the bacterium in the bacteria nutritional medium under conditions to produce BC can comprise the step of producing a BC pellicle. To produce the BC pellicle, the bacterial strain is used to inoculate a bacteria nutritional medium (culture medium) as the seed culture. The initial pH value of the medium is adjusted, e.g., to a value in the range of pH 5.0-6.0.

The pH of the medium can be unregulated during culture/fermentation and may vary. Changes in pH values may vary depending on the type of sugar in the bacterial nutritional medium (e.g., for mannitol, the pH value ranges from about pH 5.0-6.0 during culture). Some sugars will increase pH of the medium, whereas others will lower pH.

The seed culture is incubated using standard incubation methods (e.g., at 30° C. and 130 rpm on a rotary shaker for 2 days), and an aliquot of this is used to inoculate a desired volume of culture medium in a culture or fermentation vessel for production of BC. The cultivation can be carried out under standard culture conditions (e.g., at pH 5.0 and 30° C. in a static incubator for 10 days). After incubation, the BC pellicle that is produced on the surface of the sugar (e.g., mannitol) culture medium is harvested and washed successively with water and 1% (w/v), aqueous NaOH at 90° C. for 15 min, and then washed by deionized water to remove all microbial product contaminants.

In one embodiment, the following sequence of preparation steps can be employed:

Prepare mannitol culture medium used for BC production which consists of 25 g/L D-mannitol, 5 g/L yeast extract and 5 g/L tryptone.

Adjust initial pH value of the medium to 5.0 by acetic acid

Sterilize mannitol culture medium in sterilizer at 121° C. and 15 psi for 15-25 min Inoculate strain from the agar plate into a conical flask containing mannitol culture medium as the seed culture.

Culture *Acetobacter xylinum* for seed liquid at 30° C. and 130 rpm on a rotary shaker for 2 days.

Transfer 6 mL of seed liquid into a 100-mL culture medium in 500-mL conical flask for production of BC (9 mL of seed liquid into a 150-mL culture medium).

Culture *Acetobacter xylinum* for BC production at initial pH 5.0 and 30° C. in a static incubator for 10 days.

Harvest BC crude pellicle produced on the surface of mannitol culture medium.

Wash BC crude pellicle successively with water and 1% (w/v), aqueous NaOH at 90° C. for 15 min, and then remove all microbial product contaminants by deionized water (BC wet pellicle).

Remove water from the BC either by air dry, oven dry or freeze dry (for BC film).

5.3 Carbon Sources for Bacterial Cellulose (BC) Production

In one embodiment, soy flour extract (SFE), which is derived from soy flour (SF), can be used as the carbon source for BC production. Soy flour extract (SFE) consists of several sugars such as fructose, glucose, sucrose, raffinose and stachyose. Any of these sugars can be used as carbon source for bacterial cellulose production.

Fructose and glucose are preferred carbon sources for BC production as compared with sucrose, raffinose and stachyose, if the pH value of the media is kept constant. After autoclaving, the fructose and glucose concentration in the SFE medium can increase several-fold and can reach, for example, 7.54 g/L from an initial concentration of 1.92 g/L. The concentration of three sugars (fructose, glucose, and sucrose) in the SFE medium that *Acetobacter xylinum* mainly consumes during the 10-day culture can be around 25 g/L.

Other sugars known in the art can also be used for production of bacterial cellulose (BC) using *Acetobacter xylinum*, e.g., maltose or galactose.

In a preferred embodiment, the carbon source, e.g., SFE, is autoclaved using standard methods known in the art. The autoclaving process splits the sucrose in the SFE to fructose and glucose. Autoclaving causes a significant decrease in sucrose concentration and an almost equivalent increase in the fructose and glucose concentration after autoclaving. As a result, there can be no change in the combined concentration of fructose, glucose and sucrose which preferably remains in the range of 23-25 g/L, before and after autoclaving. Autoclaving can be performed on the carbon source (e.g., SFE) at any suitable point known in the art, e.g., after filtering the carbon source, after it is dried, just before using it, etc. Autoclaving can be performed for 10-40 min, preferably for 25 min (an industry norm). Longer times may allow more sucrose to hydrolyze to glucose and fructose. It may also degrade raffinose and stachyose to lower sugars. Many commercially available autoclaves are built for temperature of 121° C. and pressure of 15 psi. Although in certain embodiments these temperature and pressure conditions are preferred, other suitable temperature and pressure conditions for autoclaving can be easily determined by one of skill in the art. In certain embodiments, higher temperatures will produce faster sugar degradation.

5.4 Treatment of Soy Flour Powder to Produce SFE

The method disclosed herein for SFE production is extremely inexpensive, convenient and has a high yield.

SFE can be used as an inexpensive carbon/sugar source for the bacteria nutritional medium. In one embodiment, SFE is produced by mixing soy flour (7B) powder with deionized water to produce soy flour extract (SFE). Soy flour powder can be initially soaked in water (e.g., deionized water) in a ratio of around 3:17. The pH value of the mixture can be adjusted to 4.3-4.7, preferably 4.5, using standard methods, e.g., by adding hydrochloric acid.

The mixture can be incubated, e.g., maintained at 50° C. in a water bath for 1 hr. After that, the mixture can be filtered to remove the solid contents (e.g., insoluble protein). The filtrate can be evaporated or dried to obtain the desired suitable main sugar concentration of the SFE (based only on the combined concentration of fructose, glucose and sucrose) which is around 25 g/L for BC culture. As described above, autoclaving can be performed on the SFE at any suitable point known in the art, e.g., after filtering the carbon source, after it is dried, just before using it, etc.

In other embodiment, sugars for use in the bacteria nutritional medium can be extracted from soy protein isolate (SPI) or soy protein concentrate (SPC) using methods known in the art. The remaining protein can be used for producing soy resin (Kim, J. T.; Netravali, A. N. (2010). Effect of protein content in soy protein resins on their interfacial shear strength with ramie fibers. Journal of adhesion science and technology, 24, 203-215).

5.5 Method for Producing BC

Depending on the desired yield, laboratory (small scale) or industrial scale standard methods of bacterial cell culture can be used. The bacterial strain can be inoculated into the culture medium in a suitable container containing culture medium as the seed culture. The initial pH value of the medium can be adjusted to 5.0. The seed culture can then be incubated under standard culture conditions (e.g., for 1-2 days), and a portion of the culture can be inoculated into a new culture medium for production of BC. The cultivation can then be carried out using (e.g., at pH of 5.0 and 30° C.) in a static incubator for 5-14 days.

After incubation, BC pellicles produced on the surface of the culture medium can be harvested and washed using standard methods. For example, the BC pellicles can be washed successively with water and 1% (w/v), aqueous NaOH at 90° C. for 15 min, and then washed with deionized water to remove all microbial product contaminants. The purified BC pellicles that remain after washing can be dried using standard methods until a constant weight is obtained.

In certain embodiments, BC yield can increase dramatically during the initial 3-4 days of culture, then the yield growth can decrease after several more days (e.g., 7 days) of culture. The preferred carbon sources, fructose and glucose, will be nearly used up by this time. BC yield, however, can continue to increase during the period of 7 to 10 days of culture, but with a relatively lower rate, mainly because *Acetobacter xylinum* start to consume sucrose and other sugars, which are less preferred for BC production. Also, the decreasing volume of the medium has an effect on lowering the production of BC by the bacteria.

In certain embodiments, BC yield in 100 mL SFE medium can reach 255 mg after 10 days of culture. BC yield in SFE medium can be as high as yields from using fructose and mannitol media which are generally regarded in the art as two excellent carbon sources for BC production.

Thus according to the methods of the invention, SFE can be used as an excellent and inexpensive carbon source for BC production. The yield of BC production with SFE is high and close to or even much better than those obtained with other conventional carbon sources, including mannitol, fructose, glucose, sucrose and raffinose. The economic cost of the carbon source is relatively low because SFE is a by-product of soy flour obtained from soybean which is produced in abundance throughout the world.

5.6 Production of BC Films Based 'Green' Composites Using Resins

Many types of 'green' (e.g., non-toxic, sustainable, non-petroleum based, and/or biodegradable) composites can be produced using the methods disclosed herein. For example, in one embodiment, BC-soy resin (soy protein isolate (SPI)) composite, crosslinked (e.g., glutaraldehyde (GA)-treated) BC-soy resin (SPI) composite, BC-microfibrillated MFC (or nanofibrillated NFC) cellulose composite and BC-MFC (or NFC)-soy resin (SPI) are produced.

In certain embodiments, these 'green' composites can take the form of pellicles (discs, thin sheets or small balls) or pellets (wet condition) and films or pellets (dry condition).

BC films greatly increase the mechanical properties of soy resin (SPI) materials, including modulus (stiffness) and tensile strength. MFC can be used to further enhance this effect.

In one embodiment, BC-MFC-soy resin (SPI) composites with higher moduli are provided.

In another embodiment, GA can be used for crosslinking SPI, using standard methods, to produce BC-soy resin (SPI) composites with extremely high moduli and better thermal stability than pure BC.

In one embodiment, a method is provided for producing films of BC based 'green' composites comprising the step of immersing wet BC pellicles into soy resin (SPI) aqueous solutions. BC content (i.e., ratio) in BC-soy resin composites can be adjusted by altering the time for treatment in the aqueous solution.

In one embodiment of the method, an agent can be added, e.g., microfibrillated cellulose (MFC), nanofibrillated cellulose (NFC), cellulose nanocrystals, cellulose nanowhiskers, nanoparticles, nanoclay, nanocubes (e.g., halloysite), etc. can added into the bacteria nutritional medium during fermentation/culture. During BC synthesis, the agents can be interwoven or intercalated into the BC. The BC-agent-soy resin (SPI) composite produced can have different mechanical properties, e.g., higher modulus (stiffness) than composites not comprising the agent.

To prepare a BC-MFC pellicle, MFC (e.g., 5% by weight) can be added into the culture medium, e.g., a mannitol culture media, to form homogeneous MFC-containing mannitol culture medium.

5.7 Preparation of Soy Resin (SPI) Solutions and Soy Resin (SPI) Sheets

Methods for producing BC-soy resin based composites are provided. In one embodiment, the method comprises preparing a soy protein isolate (SPI) solution. The SPI solution can be prepared using standard methods, e.g., by mixing SPI with water (e.g., deionized or tap water) in a ratio of, e.g., 1:15. The ratio can be between 1:10 to 1:25, depending on the viscosity desired.

Glycerol may be added (e.g., 15% by weight) as a plasticizer, and the pH value of the solution can be maintained at 8.5 by addition of sodium hydroxide (Netravali, A. N., Huang, X. and Mizuta, K., Advanced Green Composites, Advanced Composite Materials, 16, pp. 269-282, 2007; Huang, X.; Netravali, A. N. (2006). Characterization of nanoclay reinforced phytagel-modified soy protein concentrate resin. *Biomacromolecules*, 7, 2783-2789; Huang, X.; Netravali, A. N. (2007). Characterization of flax fiber reinforced soy protein resin based green composite modified with nano-clay reinforced. *Composites Science and Technology*, 67, 2005-2014). The solution can be maintained, e.g., at 95° C. while stirring continuously for 40 min, to obtain pre-cured soy resin (SPI) solution. This 'precuring' process helps to denature the globular protein by opening up the molecules. Pre-cured soy resin (SPI) can be cast and dried using standard methods, e.g., cast on Teflon® coated glass plates and dried in a 35° C. air circulated dry oven for 16 hr. Dried soy resin (SPI) sheet can be cured using standard methods, e.g., using a Carver Hydraulic hot press (model 3981-4PROA00, Wabash, Ind.) at 120° C. for 25 min under a pressure of 12.5 MPa. The cured soy resin (SPI) sheet can then be conditioned at ASTM conditions, e.g., 21° C. and 65% relative humidity for 3 days. The resins sheets can be assessed for their tensile properties using standard methods known in the art.

5.8 Preparation of BC-Soy Resin (SPI) and BC-MFC-Soy Resin (SPI) Composites

BC-soy resin (SPI) composites with different BC contents are provided. Such composites can be produced by using BC pellicles that are impregnated with soy resin (SPI) using ultrasonication for varying periods of time, e.g., for 2 hr, 3 hr, 8 hr and 12 hr. The wet BC-soy resin (SPI) composites can be dried using standard methods, e.g., in a 35° C. air circulating oven for 8 hr to obtain prepregs. The BC content in the BC-soy resin (SPI) will be, in certain embodiments, around 20%, 25%, 40%, and 50%, according to 2 hr, 3 hr, 8 hr and 12 hr treatments respectively.

To further modify the tensile properties of BC-soy resin (SPI), MFC can be added into the BC pellicle during the culture to produce BC-MFC-soy resin (SPI). Addition of MFC can increase tensile strain properties of BC. To produce BC-MFC-soy resin (SPI) composite, BC-MFC pellicle can impregnated into soy resin (SPI) using standard ultrasonication methods (e.g., for 12 hr). The wet BC-MFC-soy resin (SPI) composite can be dried using standard methods (e.g., in a 35° C. air circulating oven for 8 hr) to obtain pre-impregnated composite fibers ("prepregs"). The BC-MFC content in the BC-MFC-soy resin (SPI) will be, in certain embodiments, approximately 50%.

Prepregs can be cured using standard hot pressing methods (e.g., at 120° C. under a pressure of 12.5 MPa). The cured composites can be conditioned at ASTM conditions (e.g., 21° C. and 65% relative humidity for 3 days) prior to characterizing their tensile properties.

5.9 Crosslinked BC-Soy Resin (SPI) Composite

Crosslinking with a crosslinking agent can be performed on a BC-resin composite to make the composite stiffer, more insoluble, stronger, or to decrease the fracture strain or moisture absorption of the composite. Many suitable crosslinking agents are known in the art. Glutaraldehyde (GA) or glyoxal can be applied, using methods known in the art, as a crosslinking agent to a BC-resin composite, to raise the modulus of the composite. In other embodiments, rutin or quercetin can be used to crosslink amine groups in proteins in the BC-resin composite (Huang, X.; Netravali, A. N. (2006). Characterization of nano-clay reinforced phytagel-modified soy protein concentrate resin. *Biomacromolecules*, 7, 2783-2789; Huang, X.; Netravali, A. N. (2007). Characterization of flax fiber reinforced soy protein resin based green composite modified with nano-clay reinforced. *Composites Science and Technology*, 67, 2005-2014). In other embodiments, crosslinkers that react with carboxyl groups, e.g., hydroxyls, diols, ethylene glycol, can be used to crosslink BC-resin composites.

For example, wet BC-soy resin (SPI) pellicles (BC and PVA ratio=1:1) can be immersed into GA aqueous solution with a concentration of e.g., 2.5%, 5%, 7.5% or 10% (v/v). After 2 hr treatment, GA treated BC-soy resin (SPI) pellicles can be washed with water to remove the residual GA, and dried using standard methods (e.g., in a 35° C. air circulating oven for 8 hr) to obtain prepregs. The prepregs can then be cured by standard methods of hot pressing (e.g., at 120° C. under a pressure of 12.5 MPa). The cured composites were conditioned at ASTM conditions (e.g., 21° C. and 65% relative humidity for 3 days) prior to characterizing their tensile properties.

The modulus values in GA treated BC-soy resin (SPI) are raised dramatically (e.g., from 1293.76 MPa to around 3600 MPa) and the values of tensile strength and tensile strain are lowered (e.g., from 51.02 MPa and 6.22% to around 46 MPa and 1.40%) compared to those of BC-soy resin (SPI) samples without GA treatment.

5.10 Production of BC-Modified Fibers

Methods for producing fibers surface modified (e.g., coated) with bacterial cellulose (BC) are also provided. BC can be used to modify natural fibers surfaces and improve the interfacial adhesion between fiber and polymer resins, thereby forming truly 'green' fiber-reinforced composites with enhanced properties and much better durability.

Any fiber known in the art can be modified with BC. The fiber can comprise a natural cellulose-based or protein-based material selected from the group of cellulose-based materials consisting of cotton, linen, sisal, ramie, hemp, and bamboo, or from the group of protein-based materials consisting of wool, silk, angora, cashmere, mohair, alpaca, milk protein or soy protein.

The fiber can comprise a polymeric material such as cellulose acetate, nylon, rayon, modacrylic, olefin, acrylic, polyester, polylactic acid, polylactic-co-glycolic acid (PLGA), polyurethane, aramid (e.g. KEVLAR®), ultrahigh molecular weight polyethylene, (e.g. SPECTRA® or DYNEEMA®). The fiber can comprise carbon (e.g., carbon fiber) or glass (e.g., fiberglass).

Interfacial adhesion between BC-modified fibers and resins (e.g., SPI or soy resin) can be higher than that between corresponding untreated fibers and resins. The higher interfacial shear strength (IFSS) likely arises from the increase in roughness associated with the presence of nanoscale BC on the fiber surface and the potential for hydrogen bonding between the hydroxyl group present on the BC-modified fiber surface and functional groups in the resin.

Fiber surfaces may be modified so that BC surrounds the fibers, to improve their adhesion (interfacial properties) to a variety of resins, thereby improving the composite properties.

In certain embodiments, composites with high IFSS are provided, which are stronger and stiffer. In other embodiments, composites with low IFSS are provided, which are weaker but tougher.

In one embodiment, the method for producing BC-modified fibers can comprise inoculating a bacterial strain into a mannitol culture medium (or other suitable sugar culture medium as described herein) as the seed culture. The seed culture is incubated using standard culture methods as described herein, and inoculated into a fiber-sugar bacteria nutritional (culture) medium for production of BC-fiber composite. The cultivation is carried out using standard culture methods. After cultivation, the surface of the fiber will be coated a layer of BC. The BC-modified fiber can then be harvested and washed successively with water and 1% (w/v), aqueous NaOH at 90° C. for 15 min, and then washed by deionized water to remove all microbial product contaminants.

5.11 Preparation of Resin

Any resin known in the art can be used in the methods and compositions disclosed herein. In a specific embodiment, SPI or soy resin can be mixed with deionized or tap water in a ratio of, e.g., 1:10 to 1:20. The mixture can be homogenized and then 'pre-cured' (e.g., maintaining the mixture in a water bath at 75° C. for an 30 min). This precuring process helps denature the globular protein by opening up the molecules. The pre-cured resin can be used to make microbeads on a single fiber.

In other embodiments, BC-modified fibers can be impregnated into pre-cured resin and then clamped at both ends to ensure a high degree of alignment during composite fabrication. FIG. 12 shows a BC-Sisal-soy resin hybrid composite.

To obtain BC-modified fiber-resin with greater alignment of the fibers, silicon molds made by standard methods can be used, as shown in FIG. 13.

IFSS of the BC-modified fiber can be tested using the art-known microbond test (FIG. 9). The fiber diameter, d and embedded length, L, can be measured prior to the microbond test using a calibrated optical microscope. To obtain accurate measurements, d and L are measured again after the microbond test. The microbond test can be performed using standard, commercially available instrumentation (e.g., an Instron universal testing machine, model 5566 with a microvise). The microvise plates are placed just above a microbead and brought closer until they barely touched the fiber surface as shown in FIG. 9. The fiber being tested is then pulled out from the microbead until the microbead debonds. The interfacial shear strength, τ, is calculated using the following equation:

$$IFSS(\tau) = \frac{F}{\pi \times d \times L}$$

where F is the force required to debond the microbead. For purposes of calculation, it can be assumed that the shear strength is uniform along the entire fiber/microbead interface.

5.12 Production of Films BC-Based Biocompatible Polymer Composites

Water-soluble and biocompatible (and/or biodegradable) polymers can be employed in the methods for producing 'green' composites. They enhance the properties of BC and form soft, uniform, and biocompatible composites. Poly (vinyl alcohol) (PVA) and poly (ethylene oxide) (PEO) are two kinds of thermoplastic polymers that are water-soluble, nonvolatile and biocompatible. PVA is also biodegradable. The hydrogen bonds are formed between hydroxyl groups of BC and PVA or PEO, thus further improving the uniformity and strength of the composites.

In specific embodiments, the BC-based water-soluble and biocompatible polymer composites produced according to the methods of the invention are BC-PVA and BC-PEO composites.

BC content in BC-resin composites can be adjusted by using different concentrations of aqueous solutions of the resin. The BC content can vary between 20 to 60% (by weight) of the BC-resin composite, depending on the desired application, with higher BC content resulting in stronger composites.

The inclusion of BC in resin materials can greatly increase their mechanical properties, including modulus (stiffness) and tensile strength, because hydrogen bonds can form between hydroxyl groups of BC and the resin. The BC-based water-soluble and biocompatible polymer composites such as BC-PVA and BC-PEO have better thermal stability than that of pure BC. These composites have smooth surfaces and uniform thicknesses. Resin not only penetrates into the BC network, but also fills in pores among the nanofibers formed by the BC network.

In other embodiments, BC can be used to make membrane-like composites that can be used "as is" or can be added to another composite to improve the properties of the composite. In addition to PVA and PEO, other 'green' or biodegradable resins such as soy protein resins or starch can be used.

In other embodiments, 'non-green' resins such as epoxies, unsaturated polyester, polyurethane, vinyl ester, etc. can also be used. In certain embodiments, a resin can be transparent, and the resulting BC-modified resin can be used in applications in which strong or durable transparent materials such as glass or transparent thermoplastic are generally used.

In one embodiment, a method is provided for producing films of BC-based 'green' composites comprising the step of immersing wet BC pellicles into an aqueous resin solution. The BC-based composites produced by the method have smoother surfaces and more uniform thicknesses, and their mechanical properties and thermal properties are better than composites previously achieved in the art.

5.13 Methods for Producing Films of BC-Resin Composites

Methods for producing films of BC-resin composites are provided. In one embodiment, an aqueous solution of resin powder (e.g., PVA powder) is prepared using standard methods. Purified BC pellicles are immersed into the resin solution under standard conditions known in the art (e.g., in an 80° C. water bath for 2 hr). The BC pellicles are immersed in the resin solution at room temperature (e.g., for 12 hr). The resin-containing BC pellicle is then transferred into deionized water for 30 min to remove superfluous resin on the surface of the BC pellicle and to stabilize the BC-resin composite. The film of BC-resin composite is dried using standard methods until a constant weight was obtained.

In one embodiment, the mean diameter of BC-modified nanofibers is less than 100 nm and the diameter of pore ranges from several dozens to several hundred nanometers.

5.14 Methods for Characterizing Bacterial Cellulose (BC) Based 'Green' Composites BC based green composites can be characterized using standard methods of scanning electron microscopy (SEM), tensile testing, moisture content testing, etc.

Samples of BC based green composites can be characterized by a Fourier transform infrared spectrometer for the evaluation of chemical structures.

Thermogravimetric analysis (TGA, TA instrument) can carried out to characterize the thermal properties of samples.

Interfacial shear strength (IFSS) between BC-modified fibers and resins can be tested by using the art-known methods, such as the microbond test.

5.15 Uses for Bacterial Cellulose Based 'Green' Composites

The BC based green composites can have many uses, including but not limited to: components of electronics (circuit boards), components of microphones and speakers (e.g., diaphragms), wound dressings, scaffolds for tissue engineering, synthetic dura mater (brain covering), bladder neck suspension, soft tissue replacement, artificial blood vessels, diet foods and other foods (e.g., nata de coco), matrices for electronic paper, reinforcement for paper, tape or other adhesives, automotive components (e.g., automobile body, many reinforced plastic body parts), aerospace components (airplanes, rockets, etc.), building materials (construction poles, walls, etc.) to sporting goods (tennis or badminton rackets, ski poles, fishing rods, etc.), packaging and other applications in which biodegradable membranes are desirable.

In other embodiment, fully transparent composites (made with transparent resins) can be used in place of glass in many applications to reduce weight (e.g., buildings, automobiles, airplanes, etc.).

The following examples are offered by way of illustration and not by way of limitation.

6. EXAMPLES

6.1 Example 1

**Low Cost Carbon Source from Soy Flour for Bacterial Cellulose (BC) Production by the *Acetobacter xylinum***

This example demonstrates the successful development from defatted soy flour of a low-cost carbon source for production of bacterial cellulose (BC) using *Acetobacter xylinum*. Soy flour extract consists of several sugars such as fructose, glucose, sucrose, raffinose and stachyose. All of them can be used as carbon source for bacterial cellulose production. The example demonstrates that *Acetobacter xylinum* prefer consuming sugars in the following order: fructose and glucose, sucrose, and raffinose and stachyose during the culture process. Results also indicated that the autoclaving process resulted in splitting sucrose to fructose and glucose. Based on the same concentration of sugars (25 g/L) in the culture media, bacterial cellulose yield using soy flour extract medium (based only on the concentration of fructose, glucose and sucrose) was close to or even higher than the yields obtained using conventional carbon sources media such as glucose, fructose and mannitol.

Introduction

A low-cost carbon source, soy flour extract (SFE), was developed from soy flour (SF) for BC production. The sugars were extracted by solubilizing them in water while keeping the protein insoluble (Kim, J. T.; Netravali, A. N. 2010. Mechanical, Thermal, and Interfacial Properties of Green Composites with Ramie Fiber and Soy Resins. *Journal of Agricultural and Food Chemistry*. DOI: 10.1021/jf100317y.)

The method of SFE preparation was extremely inexpensive and convenient and the results indicated that the BC production yield was comparable to those obtained by other researchers using other carbon sources. The consumption of different sugars by Acetobacter xylinum and the compositional changes of sugars in the SFE medium during autoclaving were analyzed as well.

Materials and Methods

Microorganism and Culture Media

*Acetobacter xylinum*, ATCC 23769, obtained from the American Type Culture Collection (ATCC, Manassas, Va.) was used as the model strain and maintained on agar plates containing 25 g/L D-mannitol, 5 g/L yeast extract and 5 g/L tryptone and 20 g/L agar. The SFE medium used for BC production consisted of 5 g/L yeast extract, 5 g/L tryptone and the autoclaved SFE as the sole carbon source. Other culture media used for comparison of BC yields consisted of 25 g/L carbon sources (including raffinose, glucose, sucrose, fructose and mannitol respectively), 5 g/L yeast extract and 5 g/L tryptone.

Treatment of Soy Flour Powder

Soy flour (7B) powder obtained from ADM Co. (Decatur, Ill.) was mixed with deionized water to produce soy flour extract (SFE). Soy flour powder was initially soaked in deionized water in a ratio of 3:17 and pH value of the mixture was adjusted to 4.5 by adding hydrochloric acid. The mixture was maintained at 50° C. in a water bath for 1 hr. After that, the mixture was filtered to remove the solid contents, mostly the insoluble protein. Part of the filtrate was then allowed to evaporate to obtain the desired suitable main sugar concentration (based only on the concentration of fructose, glucose and sucrose) which was around 25 g/L (preferred concentration) for BC culture. Other main sugar concentrations between 15 and 30 g/L can also be used (with lower concentration resulting in lower BC production and vice versa).

Consumption of Sugars in SFE Medium

The concentrations of sugars, including fructose, glucose, sucrose, raffinose and stachyose were determined before and after autoclaving using art-known methods of high performance liquid chromatography (HPLC) using an UltiMate 3000 LC system (Dionex, Sunnyvale, Calif.) attached with the refractive index (RI) detector (RI-101, Ecom, Purage, Czech Republic). Autoclaving of the SFE was carried out at 121° C. and 15 psi in a sterilizer (Market forge, Alfa Medical, Westbury, N.Y.) for 25 min. After removing big protein deposits, the autoclaved SFE was used for BC culture. Sugar concentrations in the SFE during 10 days of culture were determined on a daily basis using HPLC. After filtering the samples through a 0.45 µm pore size polytetrafluoroethylene (PTFE) filter and removing tiny BC fibrils and other impurities in the SFE medium, each sugar concentration was analyzed with a SUPELCOSIL LC-$NH_2$ column (25 cm×4.6 mm ID and 5 µm particles, Supelco, Bellefonte, Pa.) and the RI detector. The HPLC column was used at 30° C. temperature. The mobile phase was the mixture of acetonitrile and deionized water (3:1, v/v) and was maintained at a flow rate of 1 ml/min.

Production of BC

The strain was inoculated into a conical flask containing the above mentioned SFE culture medium as the seed culture. The initial pH value of the medium was adjusted to 5.0 and was not regulated during the culture. The seed culture was incubated at 30° C. and 130 rpm on a rotary shaker for 2 days, and 6 mL of this was inoculated into a 100-mL culture medium in a 600 ml conical flask for production of BC. The cultivation was carried out initially at pH of 5.0 and 30° C. in a static incubator for 10 days. Samples were taken from the SFE medium every day during the 10-day culture to measure the consumption of sugars and BC yields.

BC Harvesting and Weighing

After incubation, the BC pellicles produced on the surface of SFE medium and other culture media mentioned in section 2.1 were harvested every day and washed successively with water and 1% (w/v), aqueous NaOH at 90° C. for 15 min, and then washed by deionized water to remove all microbial product contaminants. The remaining purified cellulose pellicles were finally dried at 105° C. on a Teflon® plate until constant weight was obtained. BC pellicles cultured in SFE medium and other culture media mentioned in section 2.1 were compared for their yields.

Results and Discussion

Influence of Autoclaving on SFE Medium

The HPLC analysis of the crude SFE used in this study showed that it consisted of 1.92 g/L fructose and glucose (combined), 21.21 g/L sucrose, 1.59 g/L raffinose, 11.92 g/L stachyose, water and other components including proteins. The concentration of total sugars was over 36 g/L. After autoclaving (sterilizing) at 121° C. and 15 psi for 25 min, however, the HPLC analysis showed a slightly different composition of sugars in the SFE medium. Therefore, the influence of autoclaving on the SFE medium was investigated.

Sucrose is prone to heat degradation during autoclaving and that the sucrose-containing media sterilization will result in a mixture of D-glucose, D-fructose and sucrose (Dobbs, J. H.; Roberts, L. W. (1995). Experiments in plant tissue culture, third edition. *Cambridge Press*, pp. 53). 15% to 25% of the sucrose may hydrolyze to glucose and fructose during autoclaving at the elevated temperature (Ball, E. (1953). Hydrolysis of Sucrose by Autoclaving Media, a Neglected Aspect in the Technique of Culture of Plant Tissues. *Bulletin of the Torrey Botanical Club,* 80(5), 409-411; Schenk, N.; Hsiao, K. C.; Bornman, C. H. (1991). Avoidance of precipitation and carbohydrate breakdown in autoclaved plant tissue culture media. *Plant Cell Reports,* 10(3), 115-119).

Table 1 presents the HPLC data for various sugar concentrations in SFE before and after autoclaving. Table 1 also gives adjusted values for all sugars after considering the water evaporation during autoclaving. Before autoclaving, the crude SFE medium had concentrations of 1.92 g/L for fructose and glucose, 21.21 g/L for sucrose, 1.59 g/L for raffinose, and 11.92 g/L for stachyose. After the autoclaving the concentrations changed to 7.54 g/L for fructose and glucose, 17.54 g/L for sucrose, 1.58 g/L for raffinose and 9.92 g/L for stachyose. The concentration of total sugars was 36.58 g/L and the concentration of three traditional carbon sources (fructose, glucose and sucrose) for BC production was approximately 23-25 g/L which was almost the same as the regular concentration of carbon source used for BC production by others (Hong, F.; Qiu, K. (2008). An alternative carbon source from konjac powder for enhancing production of bacterial cellulose in static cultures by a model strain *Acetobacter aceti* subsp. *xylinus* ATCC 23770. *Carbohydrate Polymers,* 72 (3), 545-549).

TABLE 1

Effect of autoclaving on the concentrations of various sugars in the SFE medium

| | Concentrations of sugars in SFE medium | | | | |
|---|---|---|---|---|---|
| | Fructose and Glucose (g/L) | Sucrose (g/L) | Raffinose (g/L) | Stachyose (g/L) | Total Sugars (g/L) |
| SFE before autoclave | 1.92 | 21.21 | 1.59 | 11.92 | 36.64 |
| SFE after autoclave | 7.54 | 17.54 | 1.58 | 9.92 | 36.58 |
| SFE after autoclave (adjusted data by considering water evaporation factor) | 7.16 | 16.66 | 1.50 | 9.42 | 34.74 |

The data in Table 1 indicate that there was a significant decrease in sucrose concentration and an almost equivalent increase in the fructose and glucose concentration after autoclaving. As a result, there was no change in the combined concentration of fructose, glucose and sucrose which remained in the range of 23-25 g/L, before and after autoclaving. As discussed earlier, this was mainly due to the degradation of sucrose (Dobbs, J. H.; Roberts, L. W. (1995). Experiments in plant tissue culture, third edition. *Cambridge Press,* pp. 53; Ball, E. (1953). Hydrolysis of Sucrose by Autoclaving Media, a Neglected Aspect in the Technique of Culture of Plant Tissues. *Bulletin of the Torrey Botanical Club,* 80(5), 409-411; Schenk, N.; Hsiao, K. C.; Bornman, C. H. (1991). Avoidance of precipitation and carbohydrate breakdown in autoclaved plant tissue culture media. *Plant Cell Reports,* 10(3), 115-119). The data also indicated that the concentration of stachyose and raffinose decreased a little during the autoclaving process (Table 1). This may be owing to hydrolysis of raffinose and stachyose similar to that of sucrose. In experiments on pure rafffinose and stachyose, they were not observed to degrade during the short time of autoclaving (although hydrolysis is a possibility). During autoclaving, raffinose and stachyose may hydrolyze as sucrose does. The reduction of raffinose and stachyose in SFE medium during autoclaving may be also due to a side reaction such as caramelization or maillard reaction. Other suitable temperature and pressure conditions for autoclaving can be easily determined by one of skill in the art. In certain embodiments, higher temperatures will produce faster sugar degradation.

Sugar Consumption in SFE Medium During Culture

All five sugars in SFE, fructose, glucose, sucrose, raffinose and stachyose, could be used as carbon sources separately for BC culture by *Acetobacter xylinum* and different sugars had different effectiveness for BC yields. To measure the actual consumption of individual sugars in the culture medium was analyzed for the sugar content every day.

FIG. 1 shows plots of the change in concentrations of all five sugars as a function of culture time in days. Based on the plots, fructose and glucose concentration decreased steadily and almost linearly until day 7. During that period the other sugar concentrations remained more or less stable. After the sixth day the sucrose concentration started to decrease. When fructose and glucose concentration decreased to a relatively low value (around 1.09 g/L) from initial 7.54 g/L, the *Acetobacter xylinum* started to consume sucrose. These results indicate that the *Acetobacter xylinum* preferred to consume fructose and glucose before the other three sugars present in the SFE medium. During the entire 10-day culture time, very little or no raffinose and stachyose were consumed and no significant change was noticed in their concentrations.

BC Yield in SFE Medium

BC yield in fructose or glucose media is higher than in sucrose medium (Yang, Y. K.; Park, S. H.; Hwang, J. W.; Pyun, Y. R.; Kim, Y. S. (1998). Cellulose production by *Acetobacter xylinum* BRCS under agitated conditions. *Journal of Fermentation and Bioengineering,* 85(3), 312-317). The plot of BC yield in the data presented FIG. 2 confirms that fructose and glucose were better carbon sources for BC production as compared with sucrose, raffinose and stachyose, if the pH value of the media were kept constant. After autoclaving, the fructose and glucose concentration in the SFE medium reached 7.54 g/L from the initial concentration of 1.92 g/L. The higher fructose and glucose concentration was beneficial for BC culture. It is important to note that the concentration of three sugars (fructose, glucose and sucrose) in the SFE medium, that *Acetobacter xylinum* mainly consumed during the 10-day culture, was around 25 g/L which was the same as the regular concentration of conventional carbon sources used by other researchers for BC production (Hong, F.; Qiu, K. (2008). An alternative carbon source from konjac powder for enhancing production of bacterial cellulose in static cultures by a model strain *Acetobacter aceti* subsp. *xylinus* ATCC 23770. *Carbohydrate Polymers,* 72 (3), 545-549).

FIG. 2 shows a plot of BC yield in SFE medium as a function of culture time in days. As seen in FIG. 2, BC yield increased dramatically during the initial 3-4 days and then the yield growth significantly decreased after 7 days' of culture. The main reason for this was that the preferred carbon sources, including fructose and glucose, were almost used up at this time. BC yield, however, continued to increase during the period of 7 to 10 days but with a relatively lower rate because *Acetobacter xylinum* started to consume sucrose and other sugars which were not as suitable as fructose and glucose for BC production. The results in FIG. 2 also indicate that BC yield in SFE can reach 255 mg after 10 days of culture and this value is close to or even better than BC yields with other conventional carbon sources under similar culture conditions (Keshk, S.; Sameshima, K. (2005). Evaluation of different carbon sources for bacterial cellulose production. *African Journal of Biotechnology,* 4(6), 478-482; Hong, F.; Qiu, K. (2008). An alternative carbon source from konjac powder for enhancing production of bacterial cellulose in static cultures by a model strain *Acetobacter aceti* subsp. *xylinus* ATCC 23770. *Carbohydrate Polymers,* 72 (3), 545-549). FIG. 3 compares BC yields by using different carbon sources individually after 10 days of culture. BC yield in SFE medium (255 mg) was almost as high as those using fructose (270.3 mg) and mannitol (276.3 mg) media which previously were regarded as two excellent carbon sources for BC production. Based on the data, it was concluded that SFE could be used as an excellent and one of the least expensive carbon sources for BC production. BC yield in SFE medium was also much higher than those in raffinose (29.7 mg), sucrose (72.8 mg) and glucose (128.2 mg) media. Glucose was reported as an excellent carbon source for BC production (Keshk, S.; Sameshima, K. (2005). Evaluation of different carbon sources for bacterial cellulose production. *African Journal of Biotechnology,* 4(6), 478-482) but the yield was lower in our pure glucose medium because the pH value of the medium was not regulated and gluconic acid generated by glucose during the culture caused pH value changed to less 3.5 which was not suitable for BC production. However, the glucose in SFE medium still could be used as a good carbon source because pH value in SFE medium did not change significantly during the culture. The reason might be that relatively low amount of gluconic acid was formed possibly due to several other sugars being present creating a buffer effect in the SFE medium.

The BC yield in SFE medium (255 mg) was also higher than previously reported BC yields by using konjac powder hydrolyzate (212 mg, *Acetobacter xylinum*-ATCC 23770, 8 days) and processed rice bark (242 mg, *Acetobacter xylinum*-ATCC 23769, 10 days) (Hong, F.; Qiu, K. (2008). An alternative carbon source from konjac powder for enhancing production of bacterial cellulose in static cultures by a model strain *Acetobacter aceti* subsp. *xylinus* ATCC 23770. *Carbohydrate Polymers,* 72 (3), 545-549; Goelzer, F. D. E.; Faria-Tischer, P. C. S.; Vitorino, J. C.; Sierakowski, Maria-R.; Tischer, C. A. Production and characterization of nanospheres of bacterial cellulose from *Acetobacter xylinum* from processed rice bark. (2009). *Materials Science and Engineering, C: Materials for Biological Applications,* 29(2), 546-551).

Conclusion

The results of this example demonstrate that SFE can be an excellent carbon source for BC production. The yield of BC production with SFE was high and close to or even much better than those obtained with other conventional carbon sources, including mannitol, fructose, glucose, sucrose and raffinose. The economic cost of the carbon source is relatively low because SFE is a by-product of soy flour obtained from soybean which is produced in abundance throughout the world.

The example also demonstrates that SFE contains at least five sugars and all of them can be used as carbon sources for BC production. In addition, the example demonstrates that autoclaving process can result in the change of the composition of sugars in SFE owing to hydrolysis of higher sugars.

The results also demonstrate that Acetobacter xylinum prefers to consume fructose and glucose before sucrose and other carbon sources during the culture. When the concentration of fructose and glucose is relatively low, Acetobacter xylinum then starts to consume sucrose more. Although it was seen that Acetobacter xylinum can consume raffinose and stachyose, the consumption rates were very low. Moreover, the results show that the rate of BC production is much higher when the concentration of fructose and glucose is high.

6.2 Example 2

Production of BC Films Based 'Green' Composites by Using Soy Resin

This example demonstrates the production of films of bacterial cellulose (BC) based 'green' composites, including BC-soy resin (soy protein isolate (SPI)) composite, glutaraldehyde (GA)-treated soy resin (SPI) composite, BC-microfibrillated cellulose (MFC) composite and BC-MFC-soy resin (SPI). These composites had smooth surfaces and uniform thicknesses. SEM images indicated that MFC penetrated into the network of BC nanofibers. Tensile test indicated that BC films could greatly increase the mechanical properties of soy resin (SPI) materials, including modulus and tensile strength. MFC could further enhance this effect, so that BC-MFC-soy resin (SPI) composites with higher moduli were obtained. Also, an extremely high modulus for BC-soy resin (SPI) composite could be achieved by using GA for crosslinking FTIR testing showed the presence of amino and carboxyl groups in BC-soy resin (SPI) and BC-MFC-soy resin (SPI) composites. TGA showed that BC-soy resin (SPI) composites had better thermal stabilities than pure BC.

Introduction

During past several decades, new advanced composites with excellent mechanical properties have been developed and used as metal replacements. However, most composites are made using synthetic non-degradable fibers, such as carbon, aramid and glass and polymers (resins), such as polyetheretherketone (PEEK) and epoxy. These composites pose serious solid waste disposal problems due to decreasing landfill space, widespread litter and pollution of marine environments (Chou, T. W., Frank, K. K. (1989) Composite materials series, 3, Textile structural composites. *Elsevier science publishers, New York,* 1-26; Mohanty, A. K.; Khan, Mubarak A.; Hinrichsen, G. (2000) Surface modification of jute and its influence on performance of biodegradable jute—fabric/Biopol composites. *Composites science and technology,* 60 (7), 1115-1124). As a result, biodegradable and bio-based materials have attracted much attention in recent years. 'Green' composites have been previously fabricated using soy based resins reinforced with liquid crystalline high strength cellulose fibers (Netravali, A. N., Huang, X. and Mizuta, K., Advanced Green Composites, Advanced Composite Materials, 16, pp. 269-282, 2007).

Bacterial cellulose (BC) is a promising biodegradable material with broad potential for composite reinforcement. BC is can be produced by *Acetobacter xylinum*, a Gram-negative, obligately aerobic bacterium, in a nutritional fermentation medium at 30° C. for several of days. BC has the same chemical structure as other plant-based cellulose. However, BC is composed of fiber diameters of only few nanometers and displays many unique properties, including higher purity, higher crystallinity, higher degree of polymerization, higher tensile strength, higher modulus and stronger biological adaptability (Iguchi, M.; Yamanaka, S.; Budhiono, A. (2000) Bacterial cellulose—a masterpiece of Nature's arts. *Journal of materials science,* 35 (2), 261-270; Baeckdahl, H.; Helenius, G.; Bodin, A.; Nannmark, U.; Johansson, B. R.; Risberg, B.; Gatenholm, P. (2006). Mechanical properties of bacterial cellulose and interactions with smooth muscle cells. *Biomaterials,* 27 (9), 2141-2149; Klemm, D.; Schumann, D.; Udhardt, U.; Marsch, S. (2001). Bacterial synthesized cellulose—artificial blood vessels for microsurgery. *Progress in polymer science*, 26 (9), 1561-1603; Klemm, D.; Heublein, B.; Fink, H. P.; Bohn, Andreas. (2005). Cellulose: Fascinating biopolymer and sustainable raw material. *Angewandte chemie, International edition*, 44(22), 3358-3393; Fink, H. P.; Weigel, P.; Purz, H. J.; Ganster, J. (2001). Structure formation of regenerated cellulose materials from NMMO-solutions. *Progress in Polymer Science*, 26(9), 1473-1524).

BC materials have been used in a variety of applications, including artificial skin and blood vessels, binding agents, loud speaker diaphragms, paper, foods, textiles, composite membranes, etc. (Wan, Y.; Hong, L.; Jia, S.; Huang, Y.; Zhu, Y.; Wang, Y.; Jiang, H. (2006). Synthesis and characterization of hydroxyapatite—bacterial cellulose nanocomposites. *Composites science and technology*, 66 (11-12), 1825-1832; Fontana, J. D.; De Souza, A. M.; Fontana, C. K.; Torriani, I. L.; Moreschi, J. C.; Gallotti, B. J.; De Souza, S. J.; Narcisco, G. P.; Bichara, J. A.; Farah, L. F. X. (1990). Acetobacter cellulose pellicle as a temporary skin substitute. *Applied Biochemistry and Biotechnology*, 24-25, 253-264; Shibazaki, H.; Kuga, S.; Onabe, F.; Usuda, M. (1993). Bacterial cellulose membrane as separation medium. Journal of applied polymer science, 50 (6), 965-9; Svensson, A.; Nicklasson, E.; Harrah, T.; Panilaitis, B.; Kaplan, D. L.; Brittberg, M.; Gatenholm, P. (2005). Bacterial cellulose as a potential scaffold for tissue engineering of cartilage. Biomaterials, 26 (4), 419-431). Dry BC material is not suited for some applications, however, owing to its mechanical and thermal properties.

Soy proteins are biodegradable polymers and have been used in 'green' composites because of their worldwide availability and low price. Among soy proteins, soy protein isolate (SPI) is a highly refined or purified form with minimum protein content of 90% on a moisture-free basis. It is made from defatted soy flour which has had most of the non-protein components, fats and carbohydrates removed. SPI contains 18 different amino acids which have polar functional groups such as hydroxyl, amine and carboxyl groups. These functional groups have the potential to react with, or hydrogen bond to, natural cellulose fibers that contain hydroxyl groups (Kim, J. T.; Netravali, A. N. (2010). Effect of protein content in soy protein resins on their interfacial shear strength with ramie fibers. *Journal of adhesion science and technology*, 24, 203-215).

BC-resin composites have been investigated previously (Nakagaito, A. N.; Iwamoto, S.; Yano, H., Bacterial cellulose: the ultimate nano-scalar cellulose morphology for the production of high-strength composites. Applied Physics A: Materials Science and Processing (2004), Volume Date 2005, 80 (1), 93-97; Ifuku, S.; Nogi, M.; Abe, K.; Handa, K.; Nakatsubo, F.; Yano, H., Surface Modification of Bacterial Cellulose Nanofibers for Property Enhancement of Optically Transparent Composites: Dependence on Acetyl-Group DS. Biomacromolecules (2007), 8 (6), 1973-1978). High-strength composites using BC sheet impregnated with phenolic resin or acrylic resin have been developed (Nakagaito, A. N.; Iwamoto, S.; Yano, H., Bacterial cellulose: the ultimate nano-scalar cellulose morphology for the production of high-strength composites. Applied Physics A: Materials Science and Processing (2004), Volume Date 2005, 80 (1), 93-97; Ifuku, S.; Nogi, M.; Abe, K.; Handa, K.; Nakatsubo, F.; Yano, H., Surface Modification of Bacterial Cellulose Nanofibers for Property Enhancement of Optically Transparent Composites Dependence on Acetyl-Group DS. Biomacromolecules (2007), 8 (6), 1973-1978). Although useful, the resins used in art-known BC-resin composites are not biodegradable and could cause health or environmental problems.

The inexpensive 'green' resins disclosed in this example, such as modified SP, including SF, soy protein concentrate (SPC), soy protein isolate (SPI), etc., can be used to reinforce the BC and fabricate 'green' composites with high mechanical and physical properties in the proposed research.

In this example, films of BC based 'green' composites were successfully developed by immersing wet BC pellicles into soy resin (SPI) aqueous solutions. BC contents in BC-soy resin composites could be adjusted by varying the treatment time in the aqueous solution.

Microfibrillated cellulose (MFC) was added into BC pellicles during culture and BC-MFC-soy resin (SPI) composites with higher moduli were also produced.

In addition, glutaraldehyde (GA) was used as crosslinking agent for soy resin (SPI) to produce GA treated BC-soy resin (SPI) composites with higher moduli (stiffness).

The BC-green resin composites disclosed in this example had smooth surfaces and uniform thicknesses. Excellent mechanical properties and thermal properties were achieved.

Materials and Methods

Microorganism and Culture Media

*Acetobacter xylinum*, ATCC 23769, obtained from the American Type Culture Collection (ATCC, Manassas, Va.) was maintained on agar plates containing 25 g/L D-mannitol, 5 g/L yeast extract and 5 g/L tryptone and 20 g/L agar. The mannitol culture medium used for BC production consisted of 25 g/L D-mannitol, 5 g/L yeast extract and 5 g/L tryptone.

Preparation of BC Pellicle

The strain from the agar plate was inoculated into a conical flask containing mannitol culture medium as the seed culture. The initial pH value of the medium was adjusted to 5.0 and was not regulated during subsequent culture. The seed culture was incubated at 30° C. and 130 rpm on a rotary shaker for 2 days, and 6 mL of seed liquid was inoculated into 100-mL of culture medium in 600-mL conical bottle for production of BC. The cultivation was carried out at an initial pH of 5.0 and at 30° C. in a static incubator for 10 days. After incubation, the BC pellicle produced on the surface of the mannitol culture medium was harvested and washed successively with water and 1% (w/v), aqueous NaOH at 90° C. for 15 min, and then washed with deionized water to remove all microbial product contaminants.

Preparation of BC-MFC Pellicle

MFC (5% by weight) was added into mannitol culture media (described above) to form homogeneous MFC containing mannitol culture medium for use in the production of BC. After 2 days in seed culture (as described above), 6 mL of the seed liquid was inoculated into a 100-mL MFC-containing culture medium in 600-mL conical bottle for production of BC. The cultivation was carried out at an initial pH of 5.0 and at 30° C. in a static incubator for 10 days. After incubation, the BC-MFC pellicle produced on the surface of MFC-containing mannitol culture medium was harvested and washed successively with water and 1% (w/v), aqueous NaOH at 90° C. for 15 min, and then washed with deionized water to remove microbial product contaminants. During the entire washing process, the BC-MFC pellicle was treated carefully in order to avoid separation of the MFC and BC pellicle.

Preparation of Soy Resin (SPI) Solution And Soy Resin (SPI) Sheet

Desired soy resin (soy protein isolate (SPI)) was initially mixed with deionized water in a ratio of 1:15. Glycerol was added (15% by weight) as a plasticizer. The pH value of the solution was maintained at 8.5 by addition of sodium hydroxide (Netravali, A. N., Huang, X. and Mizuta, K., Advanced Green Composites, Advanced Composite Materials, 16, pp.

269-282, 2007; Huang, X.; Netravali, A. N. (2006). Characterization of nano-clay reinforced phytagel-modified soy protein concentrate resin. *Biomacromolecules*, 7, 2783-2789; Huang, X.; Netravali, A. N. (2007). Characterization of flax fiber reinforced soy protein resin based green composite modified with nano-clay reinforced. *Composites Science and Technology*, 67, 2005-2014). The solution was maintained at 95° C. while stirring continuously for 40 min to obtain pre-cured soy resin (SPI) solution. This 'precuring' process helps denature the globular protein by opening up the molecules. Pre-cured soy resin (SPI) was cast on the Teflon® coated glass plates and dried in a 35° C. air circulated dry oven for 16 hr. Dried soy resin (SPI) sheet was cured using Carver Hydraulic hot press (model 3981-4PROA00, Wabash, Ind.) at 120° C. for 25 min under a pressure of 12.5 MPa. The cured soy resin (SPI) sheet was conditioned at ASTM conditions of 21° C. and 65% relative humidity for 3 days before tensile testing.

Preparation of BC-Soy Resin (SPI) and BC-MFC-Soy Resin (SPI) Composites

BC-soy resin (SPI) composites with different BC contents were produced by using BC pellicles and impregnating them with soy resin (SPI) using ultrasonication for 2 hr, 3 hr, 8 hr and 12 hr respectively. The wet BC-soy resin (SPI) composites were dried in a 35° C. air circulating oven for 8 hr to obtain prepregs. The BC content in the BC-soy resin (SPI) were around 20%, 25%, 40% and 50% for impregnations of 2 hr, 3 hr, 8 hr and 12 hr respectively.

For BC-MFC-soy resin (SPI) composite production, BC-MFC pellicle was impregnated into soy resin (SPI) using ultrasonication for 12 hr. The wet BC-MFC-soy resin (SPI) composite was dried in a 35° C. air circulating oven for 8 hr to obtain prepregs (i.e., pre-impregnated and/or partially cured composite sheets. The BC-MFC content in the BC-MFC-soy resin (SPI) was around 50%.

All the prepregs were then cured by hot pressing at 120° C. under a pressure of 12.5 MPa. The cured composites were conditioned at ASTM conditions of 21° C. and 65% relative humidity for 3 days prior to characterizing their tensile properties.

Preparation of Glutaraldehyde (GA) Treated BC-Soy Resin (SPI) Composite

Glutaraldehyde (GA) was used as a crosslinking agent for the soy based resin. Wet BC-soy resin (SPI) pellicles (BC and SPI ratio=1:1) were immersed into GA aqueous solutions with concentrations of 2.5%, 5%, 7.5% or 10% (v/v). After 2 hr treatment, the GA treated BC-soy resin (SPI) pellicles were washed with water to remove the residual GA. They were then dried in a 35° C. air circulating oven for 8 hr to obtain prepregs. The prepregs were then cured by hot pressing at 120° C. under a pressure of 12.5 MPa. The cured composites were conditioned at ASTM conditions of 21° C. and 65% relative humidity for 3 days prior to characterizing their tensile properties.

Characterization

Scanning electron microscopy (SEM) images of dry BC-MFC film were taken with a Leica 440 scanning electron microscope. The sample was sputter coated with gold and morphology was observed by the SEM at an accelerating voltage of 15 kV.

Tensile testing was performed with a Instron tensile test machine (5566). The test specimens were prepared by cutting the membranes to 10 mm wide and 50 mm long strips using a precise cutter. Tensile testing was conducted according to ASTM D-882-02 as a standard test method for tensile elastic properties of thin plastic sheeting. Two ends of the specimens were placed between the upper and lower jaws of the instrument, leaving a gauge length of 30 mm of the specimens between the two jaws. Strain rate of the instrument was 2%/min. The Young's modulus of samples was calculated from the tensile test results.

Moisture content (MC) was measured by a commercial moisture/volatile tester (C.W. Brabender Instrument Inc.) at 105° C. for 12 hr.

FT-IR spectra were obtained using a FT-IR spectrophotometer (Magna-IR 560, Nicolet). The sample was cut into small pieces and characterized by a Fourier transform infrared spectrometer for evaluation of chemical structure.

Thermogravimetric analysis (TGA, TA instrument) was used to analyze the thermal properties of the sample. All analyses were performed within aluminum pans under a dynamic nitrogen atmosphere between 25 and 600° C. The experiments were run at a scanning rate of 20° C./min and the nitrogen flow rate was 20 mL/min.

Results and Discussion

Formation of Composites

FIG. 4 shows films of the BC-soy resin (SPI) and GA treated BC-soy resin (SPI) composites. These materials were much softer and thicker than pure BC film. Their surfaces were smooth and thicknesses were uniform.

FIG. 5 shows the wet pellicle of BC-MFC and SEM images of its surface and cross section. The thickness of the wet BC-MFC pellicle was much thicker than pure BC pellicle as MFC inserted into BC network. From SEM images, MFC was observed to be present inside of MFC.

PEG not only was coated on the surface of BC pellicles but also penetrated into the BC fiber network (Cai, Z.; Kim, J. (2010). Bacterial cellulose/poly (ethylene glycol) composite: Characterization and first evaluation of biocompatibility. *Cellulose*, 17, 83-91). The structural modification occurred as the water surrounding polyglucosan chains were displaced, including the formation of bonds between hydroxyl groups of BC and PEG, and BC and PVA (Alberto, S.; Giovanni, T.; Anna, M. B.; Erinestina, D. P.; Elena, S.; Bruni, M. (2001). Characterization of native cellulose/poly(ethylene glycol) films. *Macromolecular materials and engineering*, 286 (9), 524-538; Wang, J.; Gao, C.; Zhang, Y.; Wan, Y. (2010). Preparation and in vitro characterization of BC/PVA hydrogel composite for its potential use as artificial cornea biomaterial. *Material science and engineering C*, 30, 214-218).

Soy resin (SPI) and GA treated soy resin (SPI) also penetrated the BC network and formed bonds between hydroxyl groups of BC and functional groups of soy resin (SPI).

Tensile Test of BC Based 'Green' Composites

Previous experiment indicated that the tensile properties of BC-soy resin (soy protein concentrate (SPC)) were much worse than BC-soy resin (SPI). Therefore, tensile testing for BC-soy resin (SPI) composite was carried out in detail according to a modified ASTM D-882-02 standard test method.

FIG. 6 presents the tensile test results for BC-soy resin (SPI) composites with different BC contents. The average tensile strength for pure SPI (0% BC) and pure BC (100% BC) were 9.61 MPa and 78.87 MPa respectively. When BC was added into soy resins (SPI), the value of tensile strength of the BC-SPI increased dramatically compared with that of pure soy resin (SPI). Tensile strength increased with increasing BC content. However, addition of BC decreased average tensile strain compared to that of soy resin (SPI). The average tensile strains for pure SPI and pure BC were 102.67% and 5.66%, respectively. As the BC content increased, the value of tensile strain for BC-soy resin (SPI) did not change significantly.

To further modify the tensile properties of BC-soy resin (SPI), MFC was added into the BC pellicle during culture, thereby producing BC-MFC-soy resin (SPI). Table 2 shows the tensile properties for BC, SPI, BC-soy resin (SPI), BC-MFC and BC-MFC-soy resin (SPI). It indicates that MFC addition increases tensile strain properties of BC, but both the values of modulus and tensile strength decrease in BC-MFC composite. This was likely due to inhomogeneous distribution of MFC in BC-MFC composite. After combining BC-MFC with soy resin (SPI), the tensile strength of BC-MFC-SPI composite (1407.97 MPa) increased dramatically and was even higher than that of BC-SPI composite (1293.76 MPa). This was possibly because during preparation of the BC-MFC-SPI composite, SPI solution replaced water inside of the BC pellicle and re-arranged the distribution of MFC, and made the composite homogenous and strong.

TABLE 2

Tensile properties of BC, SPI, BC-MFC and their based composites

|  | Pure BC | Pure SPI | BC-SPI (SPI 50%) | MFC-BC | BC-MFC-SPI (SPI 50%) |
|---|---|---|---|---|---|
| Young's Modulus (MPa) | 2492.96 (240.33) | 217.31 (17.98) | 1293.76 (19.55) | 589.95 (119.32) | 1407.97 (272.98) |
| Tensile Strength (MPa) | 78.87 (10.76) | 9.61 (0.81) | 51.02 (1.48) | 33.17 (5.81) | 49.47 (11.53) |
| Tensile Strain (%) | 5.66 (1.01) | 102.67 (24.22) | 6.22 (1.26) | 8.37 (1.62) | 6.82 (1.28) |

GA crosslinking method was also employed in the study. Table 3 shows the tensile properties and moisture contents of GA-treated BC-soy resin (SPI) composites treated with different GA concentrations. As seen from the data in Table 3, the modulus values for GA treated BC-soy resin (SPI) increased dramatically from 1293.76 MPa to around 3600 MPa and the values of tensile strength and tensile strain decreased from 51.02 MPa and 6.22% to around 46 MPa and 1.40% compared to those of BC-soy resin (SPI) samples without GA treatment. The modulus, tensile strength and tensile stain showed little variation at concentrations of GA varying from 2.5%-7.5%. However, all these values decreased significantly when the sample was treated with 10% GA.

GA treatment did not alter moisture content (MC) significantly and its values for samples remained around 12%.

TABLE 3

Tensile properties and moisture content of GA treated BC-soy resin (SPI) composites

| GA Concentration (%) | Young's Modulus (MPa) | Tensile Strength (MPa) | Tensile Strain (%) | Moisture Content (%) |
|---|---|---|---|---|
| 0% GA | 1293.76 (19.55) | 51.02 (1.48) | 6.22 (1.26) | 12.40 (2.28) |
| 2.5% GA | 3625.17 (772.74) | 46.72 (9.28) | 1.40 (0.46) | 12.10 (1.45) |
| 5.0% GA | 3604.27 (427.37) | 44.61 (10.48) | 1.40 (0.32) | 12.50 (1.34) |
| 7.5% GA | 3644.97 (525.42) | 46.15 (11.67) | 1.41 (0.62) | 12.80 (1.67) |
| 10.0% GA | 2896.28 (658.26) | 25.39 (11.75) | 0.96 (0.31) | 11.60 (1.88) |

FT-IR Spectra of BC Based 'Green' Composites

FIG. 7 depicts the FT-IR spectra of BC, BC-SPI, BC-MFC and BC-MFC-SPI samples. Spectrum (a) is an FT-IR spectrum of pure BC. A band at 3345 $cm^{-1}$ was owing to the presence of O—H stretching vibration, a band at 2850 $cm^{-1}$ represented the aliphatic C—H stretching vibration, and a band at 1020 $cm^{-1}$ represented was attributed to C—O—C stretching vibrations. Spectrum (c) shows FT-IR spectrum of pure BC-MFC composite. The intensities and the width of peak at 3350 $cm^{-1}$ were larger than that of BC, since BC-MFC has many hydroxyl groups. In spectra (b) and (d), strong peaks at 1600 $cm^{-1}$ indicated that BC-SPI and BC-MFC-SPI have amino groups. Strong and broad peaks at 3340 $cm^{-1}$ indicated that BC-MFC-SPI has many hydroxyl and carboxyl groups.

Thermo-Gravimetric Analysis (TGA) Testing of BC Based 'Green' Composites

Thermo-gravimetric analysis (TGA) can be used to characterize thermal decomposition behavior. Test results of thermal stability and decomposition of BC, BC-soy resin (SPI) are shown in FIGS. 8a-b.

FIG. 8a shows that pure BC remained stable up to 220° C., with 30% weight loss at 255° C., 50% weight loss at around 275° C. and almost complete weight loss at around 575° C.

FIG. 8b shows that BC-soy resin (SPI) at a ratio of 1:1 remained stable up to 220° C., with 30% weight loss at 270° C., 50% weight loss at around 310° C. and still only less than 80% weight loss at around 600° C.

The results indicated that BC-soy resin (SPI) composite had greater thermal stability than pure BC.

Conclusion

This example demonstrates the production of films of BC based "green" composites, including BC-soy resin (SPI) composite, GA-treated soy resin (SPI) composite, BC-MFC composite and BC-MFC-soy resin (SPI). These composites had smooth surfaces and uniform thicknesses. SEM images indicated MFC penetrated into the network of BC nanofibers. Tensile testing indicated that BC film could greatly increase the mechanical properties of soy resin (SPI) materials, including modulus and tensile strength. MFC could further enhance this effect, yielding BC-MFC-soy resin (SPI) composites with higher moduli. Also, very high moduli for BC-soy resin (SPI) composites could be achieved by crosslinking using a crosslinking agent, GA. FTIR test showed the presence of amino and carboxyl groups in BC-soy resin (SPI) and BC-MFC-soy resin (SPI) composites. TGA showed that BC-soy resin (SPI) composites had better thermal stabilities than pure BC.

6.3 Example 3

Development of BC-Modified Sisal Fiber and its Interfacial Shear Strength (IFSS) with Soy Protein This example demonstrates the production of bacterial cellulose (BC) modified sisal fiber. The interfacial shear strength (IFSS) between BC-modified sisal fiber and soy protein isolate (SPI) resin was tested using the microbond test. The results indicated that the interfacial adhesion between BC-modified sisal fiber and SPI resin was approximately 18% higher than that between unmodified sisal fiber and SPI resin. The improved IFSS likely arises from the increased roughness associated with the presence of nanoscale BC on the sisal fiber surface and the potential for hydrogen bonding between the hydroxyl group present on the BC-modified fiber surface and functional groups in the SPI resin. The example also indicates that the IFSS of other fibers and resins can similarly be improved by BC surface modification.

Introduction

Natural fibers, such as sisal and ramie, have attracted much attention in recent years for their function as reinforcement in many resins. These cellulose fibers are useful in forming environmentally friendly and biodegradable composites with resins. However, the adhesion between fiber and resin can be weak (Kim, J. T.; Netravali, A. N. (2010). Effect of protein content in soy protein resins on their interfacial shear strength with ramie fibers. Journal of adhesion science and technology, 24, 203-215).

Bacterial cellulose (BC) is a promising biodegradable material with broad potential for composite reinforcement. It is produced by *Acetobacter xylinum*, a Gram-negative, obligately aerobic bacterium, in a nutritional fermentation medium at 30° C. for several days. BC has the same chemical structure as other plant-based cellulose. However, BC is composed of fibers with diameters of only few nanometers and displays many desirable properties, including higher purity, higher crystallinity, higher degree of polymerization, higher tensile strength, higher modulus and stronger biological adaptability (Iguchi, M.; Yamanaka, S.; Budhiono, A. (2000) Bacterial cellulose—a masterpiece of Nature's arts. *Journal of materials science*, 35 (2), 261-270; Baeckdahl, H.; Helenius, G.; Bodin, A.; Nannmark, U.; Johansson, B. R.; Risberg, B.; Gatenholm, P. (2006). Mechanical properties of bacterial cellulose and interactions with smooth muscle cells. *Biomaterials*, 27 (9), 2141-2149; Klemm, D.; Schumann, D.; Udhardt, U.; Marsch, S. (2001). Bacterial synthesized cellulose—artificial blood vessels for microsurgery. *Progress in polymer science*, 26 (9), 1561-1603; Klemm, D.; Heublein, B.; Fink, H. P.; Bohn, Andreas. (2005). Cellulose: Fascinating biopolymer and sustainable raw material. *Angewandte chemie, International edition*, 44(22), 3358-3393; Fink, H. P.; Weigel, P.; Purz, H. J.; Ganster, J. (2001). Structure formation of regenerated cellulose materials from NMMO-solutions. *Progress in polymer science*, 26(9), 1473-1524).

Soy proteins are biodegradable polymers and have been used in 'green' composites because of their worldwide availability and low price. Among soy proteins, soy protein isolate (SPI) is a highly refined or purified form with a minimum protein content of 90% on a moisture-free basis. It is made from defatted soy flour, which has had most of the non-protein components, fats and carbohydrates removed. SPI contains 18 different amino acids that have polar functional groups such as hydroxyl, amine and carboxyl groups. These functional groups have a potential to react or hydrogen bond to natural cellulose fibers that contain hydroxyl groups (Kim, J. T.; Netravali, A. N. (2010). Effect of protein content in soy protein resins on their interfacial shear strength with ramie fibers. *Journal of adhesion science and technology*, 24, 203-215).

BC can be used to modify natural fibers surfaces, and improve the interfacial adhesion between fiber and polymer resins for forming truly 'green' fiber reinforced composites with enhanced properties and much better durability (Pommet, M.; Juntaro, J.; Heng, J. Y. Y.; Mantalaris, A.; Lee, A. F.; Wilson, K.; Kalinka, G.; Shaffer, M. S. P.; Bismarck, A. (2008). Surface modification of natural fibers using bacteria: depositing bacterial cellulose onto natural fibers to create hierarchical fiber reinforced nanocomposites. Biomacromolecules, 9, 1643-1651); Juntaro, J.; Pommet, M.; Kalinka, G; Mantalaris, A.; Shaffer, M. S. P.; Bismarck, Alexander. (2008). Creating hierarchical structures in renewable composites by attaching bacterial cellulose onto sisal fibers. *Advanced materials*, 20, 3122-3126).

Materials and Methods

Microorganism and Culture Media

*Acetobacter xylinum*, ATCC 23769, obtained from the American Type Culture Collection (ATCC, Manassas, Va.) was used as the model strain and maintained on agar plates containing 25 g/L D-mannitol, 5 g/L yeast extract and 5 g/L tryptone and 20 g/L agar. The mannitol culture medium used for BC production consisted of 25 g/L D-mannitol, 5 g/L yeast extract and 5 g/L tryptone.

Preparation of BC-Modified Sisal Fibers

The strain from the agar plate was inoculated into a conical flask containing mannitol culture medium as the seed culture. The initial pH value of the medium was adjusted to 5.0 and was not regulated during the culture. The seed culture was incubated at 30° C. and 130 rpm on a rotary shaker (MAXQ 4450, Thermo Scientific) for 2 days, and 9 mL of this was inoculated into a 150-mL sisal-mannitol culture medium (20 sisal fibers, 12 cm length, around 0.1 g) in 1000-mL conical bottle for production of BC-sisal composite. The cultivation was carried out at initial pH 5.0, 30° C. and 105 rpm in a rotary shaker for 3 days. After incubation, the surface of sisal fiber was coated a layer of BC. The BC-modified sisal fiber was then harvested and washed successively with water and 1% (w/v), aqueous NaOH at 90° C. for 15 min, and then washed by deionized water to remove all microbial product contaminants.

Preparation of SPI Resin

SPI resin was initially mixed with deionized water in a ratio of 1:10. The mixture was homogenized using a magnetic stirrer from 15 min after which the mixture was maintained in a water bath at 75° C. for an additional 30 min. This 'precuring' process helps denature the globular protein by opening up the molecules. The pre-cured SPI resin was used to make microbeads on a single sisal fiber.

Preparation of Sisal Fiber with SPI and of BC-Modified Sisal Fiber With SPI Microbond Specimens To evaluate the IFSS of sisal fiber-SPI and BC-modified sisal fiber-SPI, the art-known microbond technique was used. To prepare a microbond specimen, a single sisal fiber or a single BC-modified sisal fiber was mounted on a paper tab and glued at both ends using cyanoacrylate glue. Using the pre-cured SPI resin, a small microdrop (microbead) was placed on the sisal fiber or BC-modified sisal fiber. The fibers with microbeads were kept at room temperatures for at least 4 h before heating at 120° C. in an air-circulating oven for 60 min to cure the resin. This curing process has been shown to cross-link soy protein (Nam, S.; Netravali, A. N. (2006). Green composites. II. Environment-friendly, biodegradable composites using ramie fibers and soy protein concentrate (SPC) resin. Fibers and polymer, 7, 380-388). All specimens used for the microbond tests were equilibrated at 21° C. and 65% relative humidity for 24 h prior to testing.

Interfacial Shear Strength (IFSS) Test

A schematic of the microbond test for IFSS is shown in FIG. 9. The fiber diameter, d and embedded length, L, were measured prior to the micro-bond test using a calibrated optical microscope. To obtain accurate measurements, d and L were measured again after the micro-bond test. It should be noted that the microdrops tended to shrink in diameter and become smaller in diameter as the water evaporated, while there was no shrinkage in the lengthwise direction, as discussed later. The microbond test was performed on an Instron universal testing machine, model 5566, with a microvise. The microvise plates were placed just above the microbead and brought closer until they barely touched the fiber surface as shown in FIG. 9. The sisal fiber or BC-modified sisal fiber was then pulled out from the microbead at a crosshead speed of 0.2 mm/min until the microbead debonded. The interfacial shear strength, τ, was calculated using the following equation:

$$IFSS(\tau) = \frac{F}{\pi \times d \times L}$$

where F is the force required to debond the microbead. It was assumed that the shear strength was uniform along the entire fiber/microbead interface. Twenty successful tests were conducted to obtain average IFSS values.

Results and Discussion

Production of BC-Modified Sisal Fibers

BC-modified sisal fibers were successfully produced in a rotary shaker after cultivation. FIG. 10 shows the BC-modified sisal fibers where BC surrounds the sisal fiber.

IFSS for Sisal Fiber with SPI and BC-Modified Sisal Fiber with SPI

FIG. 11 shows the comparison of IFSS values for sisal fiber with SPI resin and BC-modified sisal fiber with SPI resin. The IFSS values for sisal fiber with SPI and BC modified sisal with SPI were 3.033 MPa and 3.575 MPa respectively. This indicated that IFSS tended to increase when BC are coated on the surface of sisal fibers. The improved IFSS might arise from the increase in roughness associated with the presence of nanoscale bacterial cellulose on the sisal fiber surface and the potential for hydrogen bonding between the hydroxyl group present on the BC-modified sisal fiber surface and functional groups in the SPI resin.

Conclusion

BC coated sisal fibers were produced. The interfacial shear strength (IFSS) between BC-modified sisal fiber and SPI resin was tested using the microbond test. The results indicated that BC-modified sisal fiber with SPI resin had a much higher interfacial adhesion than that of sisal fiber with SPI resin. The improved IFSS may arise from the increase in roughness associated with the presence of nanoscale bacterial cellulose on the sisal fiber surface and the potential for hydrogen bonding between the hydroxyl group present on the BC-modified fiber surface and functional groups in the SPI resin.

6.4 Example 4

Development of BC-Based Membrane-Like 'Green' Composites Using Water-Soluble and Biodegradable Polymers In this example, bacterial cellulose (BC)-based membrane-like 'green' composites were produced by immersing wet BC pellicles in polyvinyl alcohol (PVA) and polyethylene oxide (PEO) aqueous solutions. The BC content in BC-PVA and BC-PEO composites could be adjusted by using different concentrations of PVA and PEO aqueous solution. These composites had smooth surfaces and uniform thicknesses. SEM images indicated PVA and PEO not only penetrated into BC network, but also filled in pores among BC-nanofibers. Tensile test indicated that the inclusion of BC greatly increases the mechanical properties of PVA and PEO in composites, including modulus (stiffness) and tensile strength. Fourier transform infrared spectroscopy (FTIR) test showed that hydrogen bond could be formed between hydroxyl groups of BC and PEO. TGA showed that BC-PVA and BC-PEO composites had much better thermal stabilities than that of pure BC.

Introduction

During the past several decades, new advanced composites with excellent mechanical properties have been developed and used as metal replacements. However, most composites are made using synthetic non-degradable fibers, such as carbon, aramid and glass and polymers (resins), such as polyetheretherketone (PEEK) and epoxy. These composites pose a serious solid waste disposal problem owing to decreasing landfill space, widespread litter and pollution of marine environments (Chou and Frank, 1989; Mohanty, A. K.; Khan, Mubarak A.; Hinrichsen, G. (2000) Surface modification of jute and its influence on performance of biodegradable jute—fabric/Biopol composites. *Composites science and technology*, 60 (7), 1115-1124). As a result, biodegradable and bio-based materials have attracted much attention in recent years. Very recently advanced 'green' composites were fabricated using soy based resins reinforced with liquid crystalline high strength cellulose fibers (Netravali, A. N.; Huang, X; Mizuta, K. (2007) Advanced 'green' composite. *Advanced composite materials*, 16 (4), 269-282).

BC is produced by *Acetobacter xylinum*, a Gram-negative, obligately aerobic bacterium, in a nutritional fermentation medium as described hereinabove. The medium at least contains carbon sources (mannitol, sucrose, fructose, etc.) and nitrogen sources (peptone, tryptone, yeast extract, etc.), and its optimum pH is 5.0. BC has the same chemical structure as other plant-based cellulose, has nanoscale fiber diameters and displays many unique properties including higher purity, higher crystallinity, higher degree of polymerization, higher tensile strength, higher modulus and stronger biological adaptability. Bacterial cellulose as a potential scaffold for tissue engineering of cartilage. *Biomaterials*, 26 (4), 419-431). However, the mechanical and thermal properties of dry BC material are not ideal for some applications.

Water-soluble and biocompatible polymers were used in this example to enhance the properties of BC and form soft, uniform, and biocompatible composites. Poly (vinyl alcohol) (PVA) and poly (ethylene oxide) (PEO) are two kinds of thermoplastic polymers that are also water-soluble, nonvolatile and biocompatible. PVA is also biodegradable. Hydrogen bonds are formed by hydroxyl groups of BC and PVA or PEO, thus further improving the uniformity of films formed by the composite. A BC-PVA composite is known in the art (Wang, J.; Gao, C.; Zhang, Y.; Wan, Y. (2010). Preparation and in vitro characterization of BC/PVA hydrogel composite for its potential use as artificial cornea biomaterial. *Material science and engineering C*, 30, 214-218), but BC content in the composite was low and its mechanical properties were not ideal for some applications.

BC-PEO or BC-PEG composites have been developed in the form of BC-PEO strings during BC culture in PEO containing medium (Brown, E. E.; Laborie, M. G. (2007). Bioengineering bacterial cellulose/poly (ethylene oxide) nanocomposites. *Biomacromolecules*, 8, 3074-3081) or in the form of BC-PEG film (Cai, Z.; Kim, J. (2010). Bacterial cellulose/poly (ethylene glycol) composite: Characterization and first evaluation of biocompatibility. *Cellulose*, 17, 83-91).

In this example, films of bacterial cellulose (BC)-based 'green' composites were produced by immersing wet BC pellicles into PVA or PEO aqueous solutions. The composites had higher PVA or PEO content than previously achieved and this content could be easily controlled as desired, e.g., ratios of 1:3, 1:2, 1:1, 2:1; 3:1 etc., for ratios of PVA or PEO:BC. BC content in BC-PVA and BC-PEO composites were adjusted by using different concentrations of PVA and PEO aqueous solution. The mechanical and structural properties of composites with BC-PVA and BC-PEO ratio were compared.

These composites had smoother surfaces and more uniform thicknesses, and their mechanical properties and thermal properties were better than composites previously achieved in the art.

Materials and Methods

Microorganism and Culture Media

*Acetobacter xylinum*, ATCC 23769, obtained from the American Type Culture Collection (ATCC, Manassas, Va.) was used as the model strain and maintained on agar plates containing 25 g/L D-mannitol, 5 g/L yeast extract and 5 g/L tryptone and 20 g/L agar. The mannitol culture medium used for BC production consisted of 25 g/L D-mannitol, 5 g/L yeast extract and 5 g/L tryptone.

Preparation of BC Pellicles

The strain from the agar plate was inoculated into a conical flask containing mannitol culture medium as the seed culture. The initial pH value of the medium was adjusted to 5.0 and was not regulated during the culture. The seed culture was incubated at 30° C. and 130 rpm on a rotary shaker for 2 days, and 9 mL of this was inoculated into a 150-mL culture medium in 1000-mL conical bottle for production of BC. The cultivation was carried out at initial pH 5.0 and 30° C. in a static incubator for 10 days. After incubation, the BC pellicle produced on the surface of mannitol culture medium was harvested and washed successively with water and 1% (w/v), aqueous NaOH at 90° C. for 15 min, and then washed by deionized water to remove all microbial product contaminants.

Preparation of Films of BC-PVA Composites

PVA powder (Aldrich) initially was added into the deionized water with a specific percentage by weight, and the mixture was then stirred at 80° C. for 20 min to form PVA solution. The purified BC pellicle was immersed into the PVA solution in an 80° C. water bath for 2 hr, and was then allowed to remain in the PVA solution at room temperature for 12 hr. The PVA containing BC pellicle was then transferred into deionized water for 30 min to remove superfluous PVA on the surface of BC pellicle and to stabilize the BC-PVA composite. The BC-PVA composite film was dried at room temperature on a Teflon® plate for 48 hr until a constant weight was obtained. The BC-PVA composites with varying BC and PVA ratios are shown in Table 4.

TABLE 4

| BC and PVA ratio in BC-PVA composite | |
|---|---|
| Concentration of PVA solution for BC pellicle treatment (w/v %) | BC and PVA ratio in composite |
| 1.5% | 3:1 |
| 2.0% | 2:1 |
| 3.2% | 1:1 |
| 4.0% | 1:2 |
| 6.0% | 1:3 |

Preparation of Films of BC-PEO Composites

PEO powder (Aldrich) was added into the deionized water at a desired percentage by weight (see Table 4). The mixture was stirred at 65° C. for 20 min to form PEO solution. The purified BC pellicle was immersed into the PEO solution, and was then allowed to stay in the PEO solution at room temperature for 12 hr. The PEO containing BC pellicle was transferred into deionized water for 30 min to remove superfluous PEO on the surface of BC pellicle and to stabilize the BC-PEO composite. The BC-PEO composite film was dried at room temperature on a Teflon® plate for 24 hr until a constant weight was obtained. The BC-PEO composites with varying BC and PEO ratios are shown in Table 5.

TABLE 5

| BC and PEO ratio in BC-PEO composite | |
|---|---|
| Concentration of PEO solution for BC pellicle treatment (w/v %) | BC and PEO ratio in composite |
| 1.3 | 2:1 |
| 2.0 | 1:1 |
| 3.0 | 1:2 |

Characterization of BC-PVA and BC-PEO Composites

Scanning electron microscopy (SEM) images were taken by a LEO 1550 FESEM. Freeze dried samples of BC, BC-PVA and BC-PEO composites were sputter coated with gold and their morphologies were observed with the LEO 1550 FESEM at an accelerating voltage of 15 kV.

Tensile testing was performed by an Instron tensile test machine (model 5566). The test specimens were prepared by cutting the membranes into 10 mm wide and 60 mm long strips using a precise cutter. Young's moduli of the samples were determined from the tensile test results conducted according to ASTM D-882-02, using standard test methods for tensile elastic properties of thin plastic sheeting. Two ends of the specimens were placed between the upper and lower jaws of the instrument, leaving a gauge length of 30 mm of the specimens between the two jaws. Strain rate of the instrument was 2%/min All samples were conditioned at 20° C. and 65% RH for 3 days prior to tensile test.

Moisture content (MC) was measured by a moisture/volatile tester (C.W. Brabender Instrument Inc.) at 105° C. for 12 hr. All samples were conditioned at 21° C. and 65% RH for 3 days prior to MC testing.

FT-IR spectra were obtained using a FT-IR spectrophotometer (Magna-IR 560, Nicolet). Samples were cut into small pieces and characterized by a Fourier transform infrared spectrometer for the evaluation of chemical structures.

Thermogravimetric analysis (TGA, TA Instrument) was carried out using standard methods. TGA was used to analyze the thermal properties of the sample. All analyses were performed in aluminum pans under a dynamic nitrogen atmosphere between 25 and 600° C. for pure BC 25 and 800° C. for BC-PVA and BC-PEO composites. The experiments were run at a scanning rate of 20° C./min and the nitrogen flow rate was 20 mL/min.

Results and Discussion

Formation and SEM Images of BC-PVA and BC-PEO

FIG. 14 shows films of BC-PVA and BC-PEO composites. The materials are much softer than pure BC film. Their surfaces were smooth and their thicknesses were uniform.

It has been reported previously that PEG may not only coat the surface of BC pellicles but may also penetrate into the BC fiber network (Cai, Z.; Kim, J. (2010). Bacterial cellulose/poly (ethylene glycol) composite: Characterization and first evaluation of biocompatibility. *Cellulose*, 17, 83-91). Furthermore, structural modification can occur as the water surrounding polyglucosan chains are displaced, including the formation of bonds between hydroxyl groups of BC and PEG and of BC and PVA (Alberto, S.; Giovanni, T.; Anna, M. B.; Erinestina, D. P.; Elena, S.; Bruni, M. (2001). Characterization of native cellulose/poly(ethylene glycol) films. *Macromolecular materials and engineering*, 286 (9), 524-538; Wang, J.; Gao, C.; Zhang, Y.; Wan, Y. (2010). Preparation and in vitro characterization of BC/PVA hydrogel composite for its potential use as artificial cornea biomaterial. *Material science and engineering C*, 30, 214-218).

Figure 15:
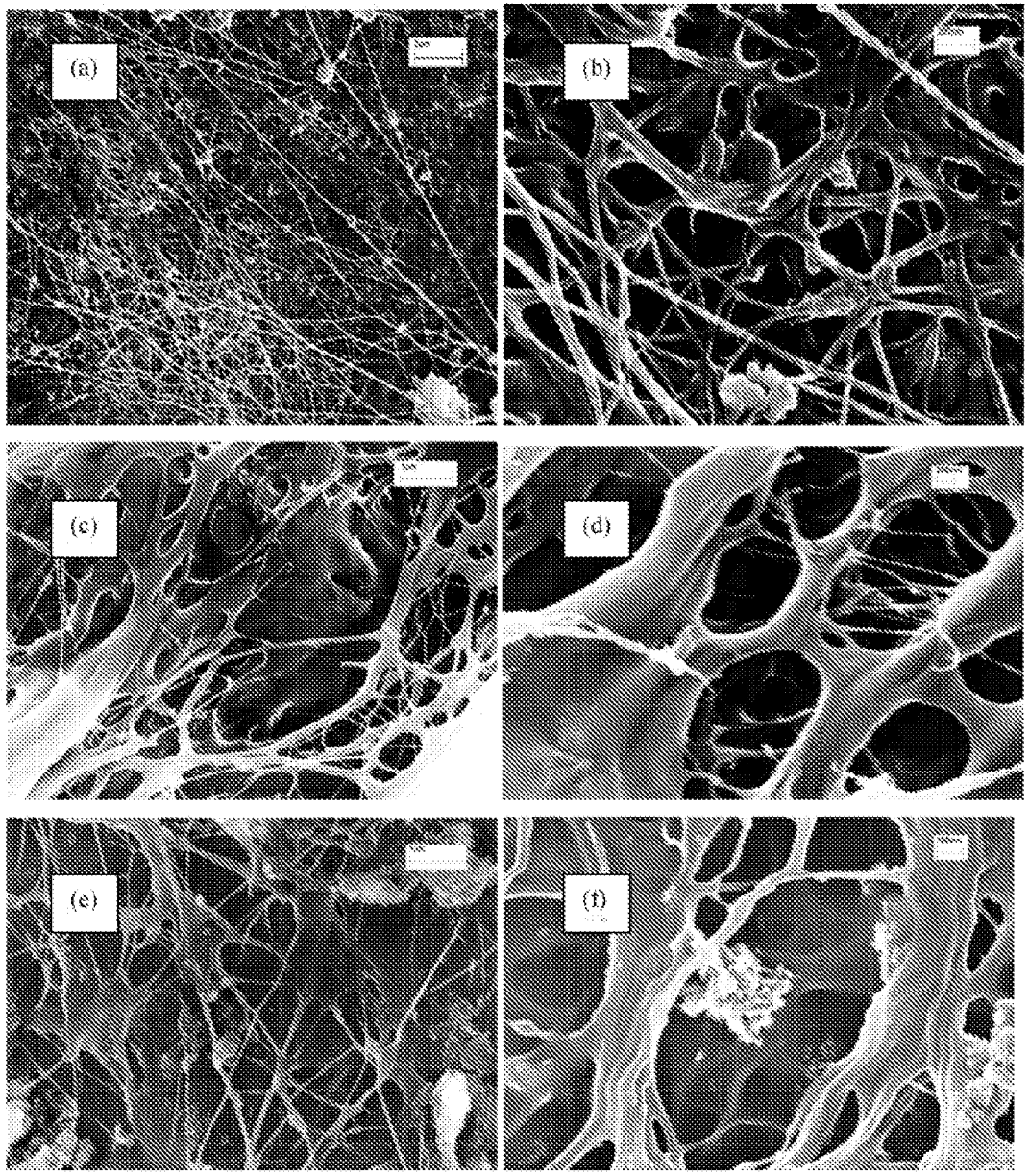

FIGS. 15*a-f* show SEM images of freeze dried pure BC, BC-PVA and BC-PEO composites. In FIGS. 15*a-b*, the BC network and porous structure can be observed clearly from the surface of the composite. The mean diameter BC-nanofibers is less than 100 nm and the diameter of pore ranges from several dozens to several hundred nanometers. FIGS. 15*c-d* show structures of BC-PVA composites. FIGS. 15*e-f* and show structures of BC-PEO composites. PVA and PEO penetrated into the BC network structure and filled in most of pores of the BC. The diameter of BC-nanofibers became larger owing to the coverage of PVA and PEO. FIG. 15*e* also shows that many BC-nanofibers were embedded within the PVA and PEO layers, thus forming uniform composite structures.

Tensile Properties and Moisture Content of BC-PVA Composites

Tensile testing of BC-PVA composites was done according to modified ASTM D-882-02 standard test methods. Table 6 presents the tensile test results for BC, PVA and BC-PVA composites at different ratios.

The mean modulus of BC was 2492.96 MPa while the mean modulus of PVA was 12.77 MPa. Mean modulus values of BC-PVA composites were between those of BC and PVA. With the increasing of BC content, the mean modulus in BC-PVA composite increased as well. While the ratio of BC-PVA was 1:3, the mean modulus was only around 751.85 MPa. When the ratio increased to 1:1, the mean modulus increased to 1590.12 MPa. It further increased to 2250.75 MPa at the ratio of 3:1, which was very close to pure BC.

Mean tensile strength at the break of BC was 78.87 MPa and that for PVA was approximately 5.36 MPa. The mean tensile strength values at break for BC-PVA composites were also between those between BC and PVA, and the values increased when BC content in the composites increased. However, tensile strength differences between different BC-PVA composites were not so obvious compared to modulus. Tensile strength ranged from 29.54 MPa when BC:PVA ratio was 1:3 to 38.97 MPa when the ratio was 3:1.

For tensile strain, the value of PVA was 234.25%, which was much higher than BC's fracture strain of 5.66%. However, the tensile strains of BC-PVA composites were lower than both those of BC and PVA. The tensile strains ranged from 1.95% at the BC-PVA ratio of 3:1 to 5.39% at the ratio of 1:3. This was likely owing to the two components in the composites having very different tensile strains.

For moisture content (MC), the value of BC was 17.80% while that of PVA was only 3.85%. With increasing BC content in the BC-PVA composite, the MC increased as well.

TABLE 6

Tensile properties and moisture contents for BC, PVA and BC-PVA composites

|  | Modulus (MPa) | Tensile strength (MPa) | Tensile strain (%) | MC (%) |
| --- | --- | --- | --- | --- |
| BC | 2492.96 | 78.87 | 5.66 | 15.60 |
|  | (240.33) | (10.76) | (1.01) |  |
| PVA | 12.77 | 5.36 | 234.25 | 3.85 |
|  | (4.63) | (0.18) | (33.62) |  |
| BC:PVA (3:1) | 2250.75 | 38.97 | 1.95 | 12.87 |
|  | (133.06) | (8.50) | (0.35) |  |
| BC:PVA (2:1) | 1685.89 | 33.47 | 2.21 | 9.77 |
|  | (71.83) | (11.33) | (0.69) |  |

TABLE 6-continued

Tensile properties and moisture contents for BC, PVA and BC-PVA composites

|  | Modulus (MPa) | Tensile strength (MPa) | Tensile strain (%) | MC (%) |
| --- | --- | --- | --- | --- |
| BC:PVA (1:1) | 1590.12 | 32.56 | 2.38 | 7.67 |
|  | (190.12) | (3.56) | (0.62) |  |
| BC:PVA (1:2) | 939.60 | 31.10 | 3.76 | 7.18 |
|  | (24.18) | (1.56) | (0.06) |  |
| BC:PVA (1:3) | 751.85 | 29.54 | 5.39 | 6.81 |
|  | (50.13) | (6.05) | (0.86) |  |

BC-PEO Mechanical Properties

Tensile testing for BC-PEO composites was done according to modified ASTM D-882-02 standard test methods. Table 7 presents the tensile test results for BC, PEO and BC-PEO composite at different ratios.

The mean modulus of BC was 2492.96 MPa while the mean modulus of PEO was 403.97 MPa. The mean modulus values of BC-PEO composites were between those of BC and PEO. With the increasing of BC content, the mean modulus in BC-PEO composite increased as well. While the ratio of BC-PEO was 1:2, the mean modulus was only around 1720.29 MPa. When the ratio increased to 1:1, the mean modulus increased to 2027.99 MPa, and it would further increased to 2275.10 MPa at the ratio of 2:1 which was very close to pure BC.

Mean tensile strength at break of BC was 78.87 MPa and that for PEO was only around 6.02 MPa. The mean tensile strength values at break for BC-PEO composites were also between those between BC and PEO, and the values increased when BC content in the composites increased.

For tensile strain, the value of PEO was 2.17%, which was much higher than BC's 5.66%. However, the tensile strains of BC-PEO composites were lower than both those of BC and PEO. They ranged from 1.35% at the BC-PEO ratio of 2:1 to 2.04% at the ratio of 1:2. This was likely owing to the two components of the composites have very different tensile strains.

As the melting point was lower than 105° C. for PEO and BC-PEO composites, moisture content for these composites was not tested.

TABLE 7

Tensile properties and moisture contents for BC, PEO and BC-PEO composites

|  | Modulus (MPa) | Tensile strength (MPa) | Tensile strain (%) |
| --- | --- | --- | --- |
| BC | 2492.96 | 78.87 | 5.66 |
|  | (240.33) | (10.76) | (0.72) |
| PEO | 403.97 | 6.02 | 2.17 |
|  | (17.55) | (0.48) | (0.20) |
| BC:PEO (2:1) | 2275.10 | 27.13 | 1.35 |
|  | (37.83) | (7.58) | (0.51) |
| BC:PEO (1:1) | 2027.99 | 26.71 | 1.65 |
|  | (119.20) | (9.56) | (0.60) |
| BC:PEO (1:2) | 1720.29 | 26.05 | 2.04 |
|  | (100.36). | (5.66) | (0.53) |

Tensile Properties Comparison Between BC-PVA and BC-PEO

Based on the results discussed above, BC pellicles can be used to increase the mechanical properties of PVA and PEO materials. At the same BC-polymer ratios, BC-PVA composites had higher modulus and tensile strength while having lower tensile strains.

Fourier Transform Infrared Spectroscopy (FT-IR) of BC-PVA

FIG. 16 shows the Fourier transform infrared (FT-IR) spectra of BC, BC-PVA composites and PVA samples. Spectrum (a) is an FT-IR spectrum of pure BC. A band at 3345 cm$^{-1}$ was owing to the presence of O—H stretching vibration. A band at 2850 cm$^{-1}$ represented the aliphatic C—H stretching vibration. A band at 1020 cm$^{-1}$ was attributed to C—O—C stretching vibrations. Spectrum (e) is an FT-IR spectrum of pure PVA. The intensities of bands at 3350 cm$^{-1}$, 2860 cm$^{-1}$ and 1070 cm$^{-1}$ are much larger than those of pure BC because the PVA have many hydroxyl groups, C—H bonds and C—O—C interactions respectively. Spectra (b), (c) and (d) show BC-PVA composites with different BC-PVA ratios. The intensities of the three bands are between those of pure BC and PVA and with increasing of BC content, the intensities of the three bands decreased. The frequencies of the C—O—C bands in BC-PVA composites also shifted a little compared to those of BC and PVA which was owing to the intermolecular interacting by hydrogen bond between hydroxyl groups of BC and PVA.

FT-IR of BC-PEO

FIG. 17 shows the FT-IR spectra of BC, BC-PEO composites and PEO samples. Spectrum (a) shows FT-IR spectrum of pure BC. A band at 3345 cm$^{-1}$ was owing to the presence of O—H stretching vibration. A band at 2850 cm$^{-1}$ represented the aliphatic C—H stretching vibration. A band at 1020 cm$^{-1}$ was attributed to C—O—C stretching vibrations. Spectrum e shows FT-IR spectrum of pure PEO. It had a strong band at 1450 cm$^{-1}$ which represented CH$_2$ scissor vibration. The band at 3350 cm$^{-1}$ was broader than that of pure BC but the intensity was lower. The intensities of bands at 2860 cm$^{-1}$ and 1070 cm$^{-1}$ were much larger than those of pure BC because the PEO have many C—H bonds and C—O—C interactions respectively. Spectra (b), (c) and (d) show BC-PEO composites with different BC-PEO ratios. The intensities of CH$_2$ scissor vibration was lower than PEO and the intensities of the O—H, C—H, C—O—C bands are between those of pure BC and PEO and with increasing of BC content, the intensities of O—H bands increased and the intensities of C—H, CH$_2$ and C—O—C bands decreased. The frequencies of the C—O—C bands in BC-PEO composites also shifted a little compared to those of BC and PEO which was owing to the intermolecular interacting by hydrogen bond between hydroxyl groups of BC and PEO.

TGA of BC-PVA and BC-PEO Composites

Thermo-gravimetric analysis (TGA) provided information on thermal decomposition behavior. Test results of thermal stability and decomposition of BC, BC-PVA and BC-PEO are shown in FIGS. 18a-c.

FIG. 18a shows that pure BC remained stable up to 220° C., and 30% weight loss was at 255° C., 50% weight loss was at around 275° C. and almost complete weight loss was at around 575° C.

FIG. 18b shows that BC-PVA at a ratio of 1:1 remained stable up to greater than 260° C., with 30% weight loss at 315° C., 50% weight loss at around 340° C. and almost complete weight loss at greater than 800° C.

FIG. 18c shows that BC-PEO at a ratio of 1:1 remained stable up to greater than 260° C., with 30% weight loss at 315° C., 50% weight loss at around 360° C. and almost complete weight loss at greater than 620° C.

The results indicated that BC-PVA and BC-PEO composites have greater thermal stability than pure BC.

CONCLUSION

In this example, films of BC-PVA and BC-PEO composites with differing BC:PVA or BC:PEO ratios were produced by immersion methods. These composites had smooth surfaces and uniform thicknesses. SEM images indicated that PVA and PEO not only penetrated into the BC network, but also filled in pores among BC nanofibers. Tensile testing indicated that BC pellicles could greatly increase the mechanical properties of PVA and PEO materials, including increasing modulus and tensile strength. FTIR testing showed that hydrogen bonds could form between hydroxyl groups of BC and PEO. TGA showed that BC-PVA and BC-PEO had greater thermal stabilities than pure BC.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A composition comprising:
    bacterial cellulose (BC); and
    a soy-based resin.
2. The composition of claim 1 that comprises 20 to 60% BC by weight.
3. The composition of claim 1 wherein the composition is crosslinked.

* * * * *